US012714363B2

(12) United States Patent
Shen et al.

(10) Patent No.: US 12,714,363 B2
(45) Date of Patent: Aug. 25, 2026

(54) SENSORS FOR PROSTHESES

(71) Applicant: The Board of Trustees of The University of Alabama, Tuscaloosa, AL (US)

(72) Inventors: Xiangrong Shen, Tuscaloosa, AL (US); MD Rejwanul Haque, Tuscaloosa, AL (US)

(73) Assignee: The Board of Trustees of The University of Alabama, Tuscaloosa, AL (US)

( * ) Notice: Subject to any disclaimer, the term of this patent is extended or adjusted under 35 U.S.C. 154(b) by 362 days.

(21) Appl. No.: 18/523,187

(22) Filed: Nov. 29, 2023

(65) Prior Publication Data

US 2024/0172993 A1 May 30, 2024

Related U.S. Application Data

(60) Provisional application No. 63/428,560, filed on Nov. 29, 2022.

(51) Int. Cl.
*A61B 5/00* (2006.01)
*A61B 90/00* (2016.01)

(52) U.S. Cl.
CPC .......... *A61B 5/4851* (2013.01); *A61B 5/6811* (2013.01); *A61B 90/06* (2016.02); *A61B 2090/064* (2016.02); *A61B 2562/0219* (2013.01); *A61B 2562/0223* (2013.01)

(58) Field of Classification Search
CPC ..... A61B 5/4851; A61B 5/6811; A61B 90/06; A61B 2090/064; A61B 2562/0219; A61B 2562/0223; G01L 1/22
See application file for complete search history.

(56) References Cited

U.S. PATENT DOCUMENTS

2013/0319135 A1* 12/2013 Okada .................. G01L 1/2206 73/862.043
2016/0089079 A1* 3/2016 Stein .................. A61B 5/0008 600/300

OTHER PUBLICATIONS

Orendurff, M.S., et al., Gait efficiency using the C-Leg. Journal of rehabilitation research and development, 2006. 43(2): p. 239.
Prinsen, E.C., et al., The influence of a user-adaptive prosthetic knee across varying walking speeds: A randomized cross-over trial. Gait & posture, 2017. 51: p. 254-260.
Thiele, J., et al., Designs and performance of microprocessor-controlled knee joints. Biomedizinische Technik/Biomedical Engineering, 2014. 59(1): p. 65-77.
Wu, M., M.R. Haque, and X. Shen, Obtaining natural sit-to-stand motion with a biomimetic controller for powered knee prostheses. Journal of healthcare engineering, 2017. 2017.

(Continued)

*Primary Examiner* — Jason M Sims
*Assistant Examiner* — Noah M Healy
(74) *Attorney, Agent, or Firm* — Meunier Carlin & Curfman LLC

(57) ABSTRACT

Devices, systems, and methods including sensors that can be used in prostheses, including powered prostheses are described herein. An example force-moment sensor includes a first block having a first curved surface; a second block having a second curved surface; an elastic element arranged between the first block and the second block; and at least one sensing element configured to measure a deflection of the elastic element.

18 Claims, 23 Drawing Sheets

(56) References Cited

OTHER PUBLICATIONS

Gupta, S., Strain gauge load cells, in Mass Metrology. 2012, Springer. p. 89-119. https://doi.org/10.1007/978-3-642-23412-5_5.
Pratt, D., et al., Load measurement in orthopaedics using strain gauges. Journal of Biomedical engineering, 1979. 1(4): p. 287-296.
Sup, F., A. Bohara, and M. Goldfarb, Design and Control of a Powered Transfemoral Prosthesis. The International Journal of Robotics Research, 2008. 27(2): p. 263-273.
Cherelle, P., et al., Design and validation of the ankle mimicking prosthetic (AMP-) foot 2.0. IEEE Transactions on Neural Systems and Rehabilitation Engineering, 2013. 22(1): p. 138-148.
Pandit, S., et al., An affordable insole-sensor-based trans-femoral prosthesis for normal gait. Sensors, 2018. 18(3): p. 706.
Rouse, E.J., L.M. Mooney, and H.M. Herr, Clutchable series-elastic actuator: Implications for prosthetic knee design. The International Journal of Robotics Research, 2014. 33(13): p. 1611-1625.
Gabert, L. and T. Lenzi, Instrumented pyramid adapter for amputee gait analysis and powered prosthesis control. IEEE Sensors Journal, 2019. 19(18): p. 8272-8282.
Lawson, B.E., et al., A Robotic Leg Prosthesis Design, Control, and Implementation. IEEE Robotics & Automation Magazine, 2014. 21(4): p. 70-81.
Wolfram Demonstrations Project brings ideas to life with over 11k interactive #WolframNotebooks for education, research, recreation & more. #WolframDemo #WolfLang Available online: http://demonstrations.wolfram.com/MagneticFieldOfACylindricalBarMagnet/ (accessed on Oct. 29, 2022).
El Hafidi, M. How Does the Magnetic Field Strength Varies with Distance Available online: https://www.researchgate.net/post/How-does-the-magnetic-field-strength-varies-with-distance/5d4ffae2aalf099a61340827/citation/download. (accessed on Oct. 29, 2022).

* cited by examiner 102
120
110
210
206
222a 102
120
110
209
210
210

Figure 2. Cylindrical bar magnet (left) and its magnetic field distribution (right) [14]

SENSORS FOR PROSTHESES

CROSS-REFERENCE TO RELATED APPLICATIONS

This application claims the benefit of U.S. provisional patent application No. 63/428,560 filed on Nov. 29, 2022, and titled "SENSORS FOR PROTHESES," the disclosure of which is expressly incorporated herein by reference in its entirety.

GOVERNMENT SUPPORT

This invention was made with government support under grant number 1351520 awarded by the National Science Foundation and grant number 1734501 awarded by the National Science Foundation. The government has certain rights in the invention.

BACKGROUND

Prostheses are commonly used as artificial replacements for body parts.

As an example, lower limb prostheses include prostheses designed to assist individuals who are missing part or all of a leg (e.g., amputees). Lower limb prostheses can be configured to replace the missing portion of leg. For example, in an individual whose leg is amputated below the knee, the prostheses can be configured to work with the existing knee joint. Alternatively, in a user whose leg is amputated above the knee, a prosthesis can be configured to replace both the missing knee and ankle joints.

The load (e.g., weight) that is placed on a prosthesis can be measured. For example, motors or other actuators can power the prosthesis in a powered prosthesis. Measuring weight on the prosthesis can be used as part of a control system for the motors/actuators of a powered prosthesis.

Therefore, what are needed are systems and methods that overcome challenges in the art of prostheses, some of which are described above.

SUMMARY

The device, system, and methods described herein provide sensors that can be used in prostheses, including powered prostheses. The sensors can be lightweight, robust, and simple to manufacture.

According to one aspect, the present disclosure relates to a force-moment sensor for a prosthetic joint. The example force-moment sensor includes a first block having a first curved surface; a second block having a second curved surface; an elastic element arranged between the first block and the second block; and at least one sensing element configured to measure a deflection of the elastic element.

In some implementations, at least one of the first curved surface and the second curved surface is configured to bend the elastic element when a force or a moment of force is applied to the force-moment sensor.

In some implementations, the first block defines a first end and a second end opposite the first end, the first end including a first flat edge, where the second curved block includes a third end and a fourth end opposite the third end, the third end including a second flat edge, and where the first and second blocks are arranged so that the first end of the first block is adjacent to the fourth end of the second block.

In some implementations, the elastic element is fixedly attached to the first end of the first block and fixedly attached to the third end of the second block.

In some implementations, the at least one sensing element includes a plurality of sensing elements. Optionally, a first sensing element and a second sensing element are arranged at opposite ends of the elastic element.

In some implementations, the at least one sensing element includes a magnetic sensor. Alternatively or additionally, the at least one sensing element includes an inertial measurement unit (IMU). Alternatively or additionally, the at least one sensing element includes a piezoelectric sensor. Alternatively or additionally, the at least one sensing element includes a force-sensitive resistor.

In some implementations, the elastic element includes carbon fiber. Alternatively or additionally, the elastic element includes fiberglass.

In some implementations, the force-moment sensor further includes a plurality of bars, each of the respective bars being attached to the first and second blocks, where the bars are configured to limit a pulling force applied to the force-moment sensor.

In some implementations, the force-moment sensor further includes a detachable adapter for operably connecting the force-moment sensor to a prosthetic device.

In some implementations, the force-moment sensor further includes a housing.

In another aspect, the present disclosure relates to a system. The example system includes: a prosthetic device including a first portion, a second portion, and a joint, the first portion and the second portion being joined by the joint; and a force-moment sensor arranged in the joint, the force-moment sensor including: a first block having a first curved surface: a second block having a second curved surface: an elastic element arranged between the first block and the second block; and at least one sensing element configured to measure a deflection of the elastic element.

In some implementations, at least one of the first curved surface and the second curved surface is configured to bend the elastic element when a force or a moment of force is applied to the force-moment sensor.

In some implementations, the first block defines a first end and a second end opposite the first end, the first end including a first flat edge, where the second block includes a third end and a fourth end opposite the third end, the third end including a second flat edge, and where the first and second blocks are arranged so that the first end of the first block is adjacent to the fourth end of the second block.

In some implementations, the elastic element is fixedly attached to the first end of the first block and fixedly attached to the third end of the second block.

In some implementations, the at least one sensing element includes a plurality of sensing elements.

In some implementations, a first sensing element and a second sensing element are arranged at opposite ends of the elastic element.

In some implementations, the at least one sensing element includes a magnetic sensor. Alternatively or additionally, the at least one sensing element includes an inertial measurement unit (IMU). Alternatively or additionally, the at least one sensing element includes a piezoelectric sensor. Alternatively or additionally, the at least one sensing element includes a force-sensitive resistor.

In some implementations, the elastic element includes carbon fiber. Alternatively or additionally, the elastic element includes fiberglass.

In some implementations, the force-moment sensor further includes a plurality of bars, each of the respective bars being attached to the first and second blocks, where the bars are configured to limit a pulling force applied to the force-moment sensor.

In some implementations, the force-moment sensor further includes a detachable adapter for operably connecting the force-moment sensor to a prosthetic device.

In some implementations, the force-moment sensor further includes a housing.

In some implementations, the system further includes a computing device configured to: receive at least one sensor signal from the at least one sensing element; and determine a quantity of a force or a moment of force applied to the force-moment sensor based on the at least one sensor signal.

In some implementations, the system further includes a computing device configured to: receive at least one sensor signal from the at least one sensing element: and distinguish between a force and a moment of force applied to the force-moment sensor based on the at least one sensor signal.

In some implementations, the system further incudes a motor configured to drive the prosthetic device, where the computing device is further configured to: control the motor based on the at least one sensor signal.

Other systems, methods, features and/or advantages will become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The accompanying drawings, which are incorporated in and constitute a part of this specification, illustrate embodiments and together with the description, serve to explain the principles of the methods and systems:

FIG. 2D illustrates a cross sectional view of the force-moment sensor illustrated in

FIG. 2A.

DETAILED DESCRIPTION

The present disclosure relates to sensors and prosthetics including sensors.

As used in the specification and the appended claims, the singular forms “a,” “an” and “the” include plural referents unless the context clearly dictates otherwise. Ranges may be expressed herein as from “about” one particular value, and/or to “about” another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

Figure 1A:
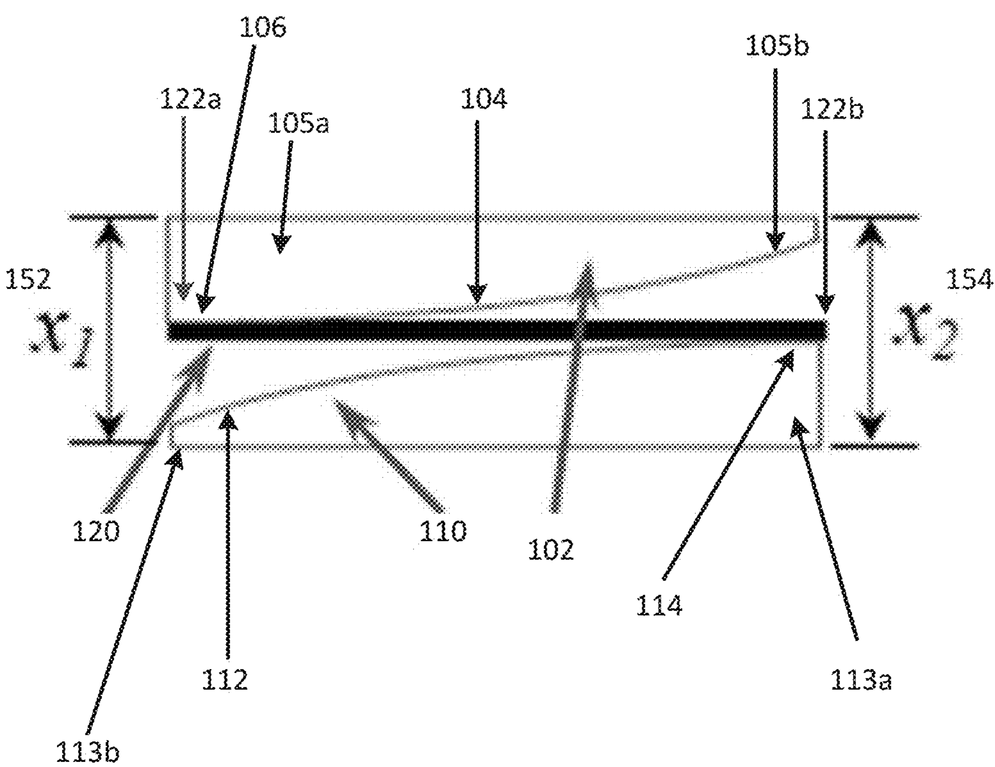
FIG. 1A illustrates a schematic of a force-moment sensor, according to one implementation of the present disclosure.

With reference to FIG. 1A, a diagram of a force-moment sensor 100 is shown. The force-moment sensor 100 includes a first block 102 with a first curved surface 104. The force-moment sensor 100 also includes a second block 110 with a second curved surface 112.

An elastic element 120 is positioned between the first block 102 and the second block 110. When the first block 102 moves towards the second block 110 (or the second block 110 moves towards the first block 102), the curved surfaces 104, 112 of each of the blocks 102, 110 can cause the elastic element 120 to bend. One or both of the blocks 102, 110 can be configured so that the forces or moments of forces on the blocks bends the elastic element relative to one or both of the blocks 102, 110.

The present disclosure contemplates that the elastic element 120 can be positioned between the first block 102 and the second block 110 using any type of attachments (e.g., brackets, etc.).

Optionally, as shown in FIG. 1A, the first block 102 and/or the second block 110 can include flat sections, referred to herein as "flat edges." The first block 102 can include a first end 105*a* and a second end 105*b*. The first end 105*a* includes a flat edge 106. The flat edge 106 of the first block 102 is then attached to the elastic element 120. Similarly, the second block 110 can include a third end 113*a* and a fourth end 113*b* on opposite sides of the second curved surface 112, and the third end 113*a* can also have a flat edge 114. The flat edge 114 on the second block 110 can also be attached to the elastic element 120. Flat edges 106 and 114 are attached at opposite ends of the elastic element 120. Accordingly, the first end 105*a* of the first block 102 can be aligned opposite the fourth end 113*b* of the second block 110, as shown in FIG. 1A. Implementations of the present disclosure including this configuration can be considered a "cantilever" structure because the elastic element 120 contacts the first and second blocks 102, 110 at only one point on each block (the flat edge 106 and flat edge 114).

The force-moment sensor 100 can include one or more sensing elements configured to measure the deflection of the elastic element 120 and thereby determine the magnitude and/or directions of the forces on the force-moment sensor 100. Nonlimiting examples of sensing elements that can be used include magnetic sensors, piezoelectric sensors, force sensitive resistors, inertial measurement units. In some implementations, multiple different types of sensing elements can be combined in the same force-moment sensor 100. Alternatively or additionally, any number of each sensing element can be used, so for example, implementations of the present disclosure can include multiple magnetic sensors in each force-moment sensor. Optionally, the different types of sensing elements can be used to measure different parameters in the sensor. Alternatively, the different parameters measured by the different sensing elements can be combined to generate a more accurate measurement of the force on the force-moment sensor 100.

Additionally, the sensing elements can be placed in different locations in/on the force-moment sensor 100. In implementations where the sensing elements is a magnetic sensor, the magnetic sensor can be configured to detect the magnetic field from a magnet. Since the magnetic field is a function of distance, the magnet and sensor can be placed on different parts of the force-moment sensor 100 so that when the elastic element 120 deflects, the magnetic field detected by the sensor changes and the force on the elastic element 120 can be determined. For example, a magnetic sensor can be located in/on the elastic element 120, and the magnet can be located on either of the curved surfaces 104, 112. Alternatively or additionally, the magnet can be located in/on the elastic element 120 and the magnetic sensor can be located in/on either of the curved surfaces 104, 112. As yet another example, the magnet can be located on one of the curved surfaces 104, 112, and the magnetic sensor can be located on the other curved surface 104, 112.

In some implementations, for the measurement of the deflections, a miniature magnet can be embedded on each end of the elastic element, and a magnetic sensor is embedded in the free end of each curved mounting block, measuring the change of the magnetic field due to the movement of the corresponding magnet. As such, the magnet sensors' signals can serve as indirect measurements of the force/moment applied to the sensor.

In some implementations, the magnetic sensor can be embedded in a small printed circuit board (PCB), which also include a signal conditioning circuit. Optionally, the output signal(s) from the magnetic sensor can be directly routed to microcontroller in the prosthesis (e.g., the computing device shown in FIG. 4). Optionally, the sensing element(s) can be configured as a plug-n-play component.

In implementations of the present disclosure including force sensitive resistors and piezoresistors, the force sensitive resistors and/or piezoresistors can be formed in/on the elastic element 120. In some implementations, the sensing element or elements are disposed on a surface of the elastic element 120. In other implementations, the sensing element or elements are embedded within the elastic element 120.

As yet another example of where the sensing elements can be located in the force-moment sensor, in some implementations the sensing elements can be located on opposite ends of the elastic elements, so that one sensing element is at the first end 122*a* of the elastic element 120 and the other sensing element is at the second end 122*b* of the elastic element 120.

The present disclosure contemplates that the elastic element 120 can be made out of any material that can deflect under pressure. Non-limiting example materials for the elastic element 120 include fiberglass and carbon fiber. It should be understood that fiberglass and carbon fiber are provided only as example materials, and that other materials can be used for the elastic element 120 in different embodiments of the present disclosure. This disclosure contemplates that the elastic element can also be made from combinations of different materials.

Figure 1B:
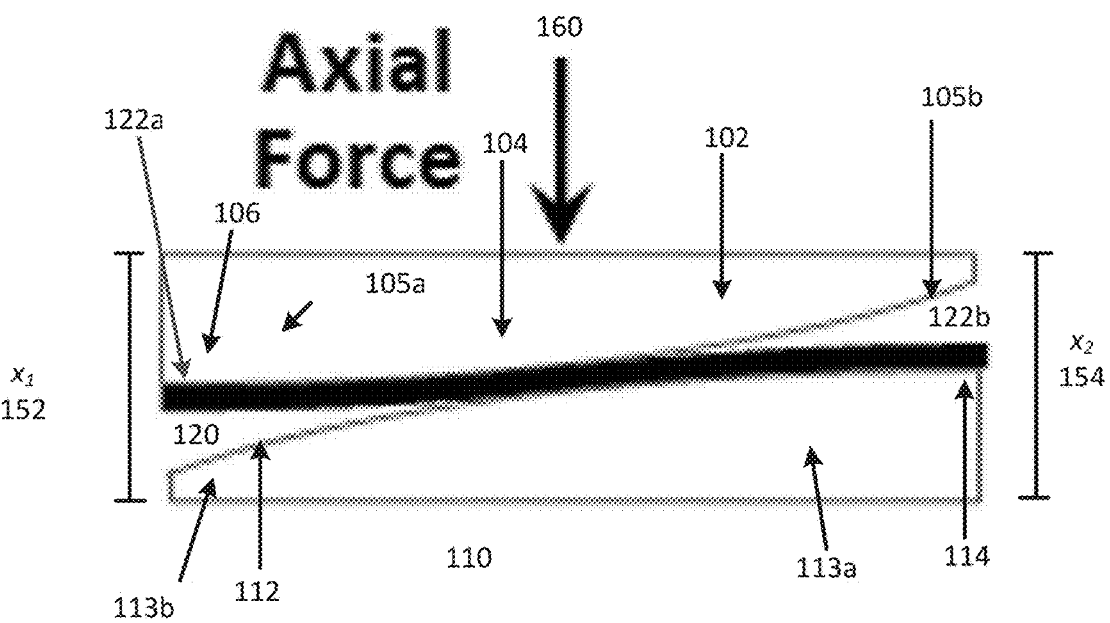
FIG. 1B illustrates the force-moment sensor shown in FIG. 1A under an axial force.

Implementations of the force-moment sensor 100 can be configured to measure the axial force and bending moment simultaneously while minimizing the mechanical complexity. As used herein, "axial force" refers to forces that are applied perpendicular to the elastic element 120. An example axial force occurs when the user is placing their weight on a prosthetic leg that the force-moment sensor 100 is used in. The axial force 160 compresses the first block 102 towards the second block 110, as shown in FIG. 1B. As used herein, "bending moment" refers to forces that twist one of the blocks 102, 110, relative to the other block. An example bending moment 170 occurs when a user is walking on the prosthetic leg and thereby using the prosthetic leg to push themselves forward relative to the ground. It should be understood that walking can include both axial force 160 and bending moment 170, because when walking the user places weight on the prosthetic, which generates axial forces 160, and also using the prosthetic to push themselves forward, causing a bending moment on parts of the prosthesis (e.g., a prosthetic knee or ankle). Different activities can generate different combinations of axial forces 160 and bending moment 170, and implementations of the present disclosure can distinguish between axial forces and bending moments.

The distances between points on the first block 102 and points on the second block 110 can be used to determine the axial forces and/or bending moment on the force-moment sensor 100, and to distinguish between the axial forces and/or bending moment on the force-moment sensor 100. As an example, the distance can be measured at opposite ends of the first block 102 and second block 110. The first distance $x_1$ 152 and second distance $x_2$ 154 are shown in FIG. 1A. FIG. 1B illustrates an example of the force-moment sensor 100 shown in FIG. 1A under an axial force 160 that deflects the elastic element. Under an axial force, the first end 122*a* and second end 122*b* experience symmetric deflections (i.e., $\Delta x_1$ 152=$\Delta x_2$ 154). Implementations of the present disclosure can measure the distances $x_1$ 152 and $x_2$ 154 to determine the bending moment using sensing elements on the first end 122*a* and second end 122*b*

Figure 1C:
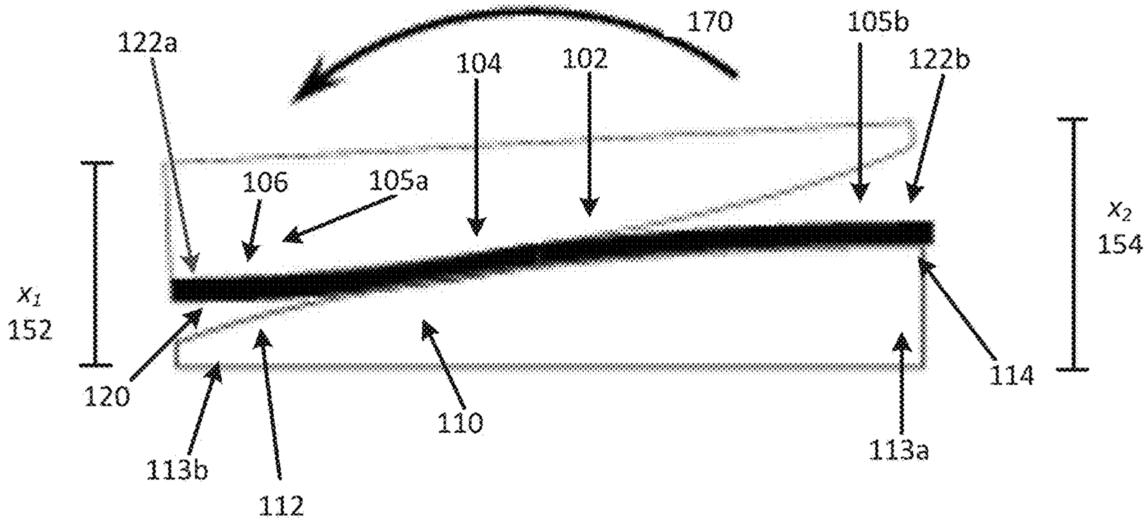
FIG. 1C illustrates the force-moment sensor shown in FIG. 1A under a bending moment.

FIG. 1C illustrates an example of the force-moment sensor 100 shown in FIG. 1A under a bending moment 170 that deflects the elastic element. Under a bending moment, the first end 122*a* and second end 122*b* experience asymmetric deflections (i.e., $\Delta x_1$ 152$\neq$$\Delta x_2$ 154).

Implementations of the present disclosure can measure any combination of the axial force and bending moment (e.g., the axial force 160 or bending moment 170 illustrated in FIGS. 1B and 1C).

Figure 2A:
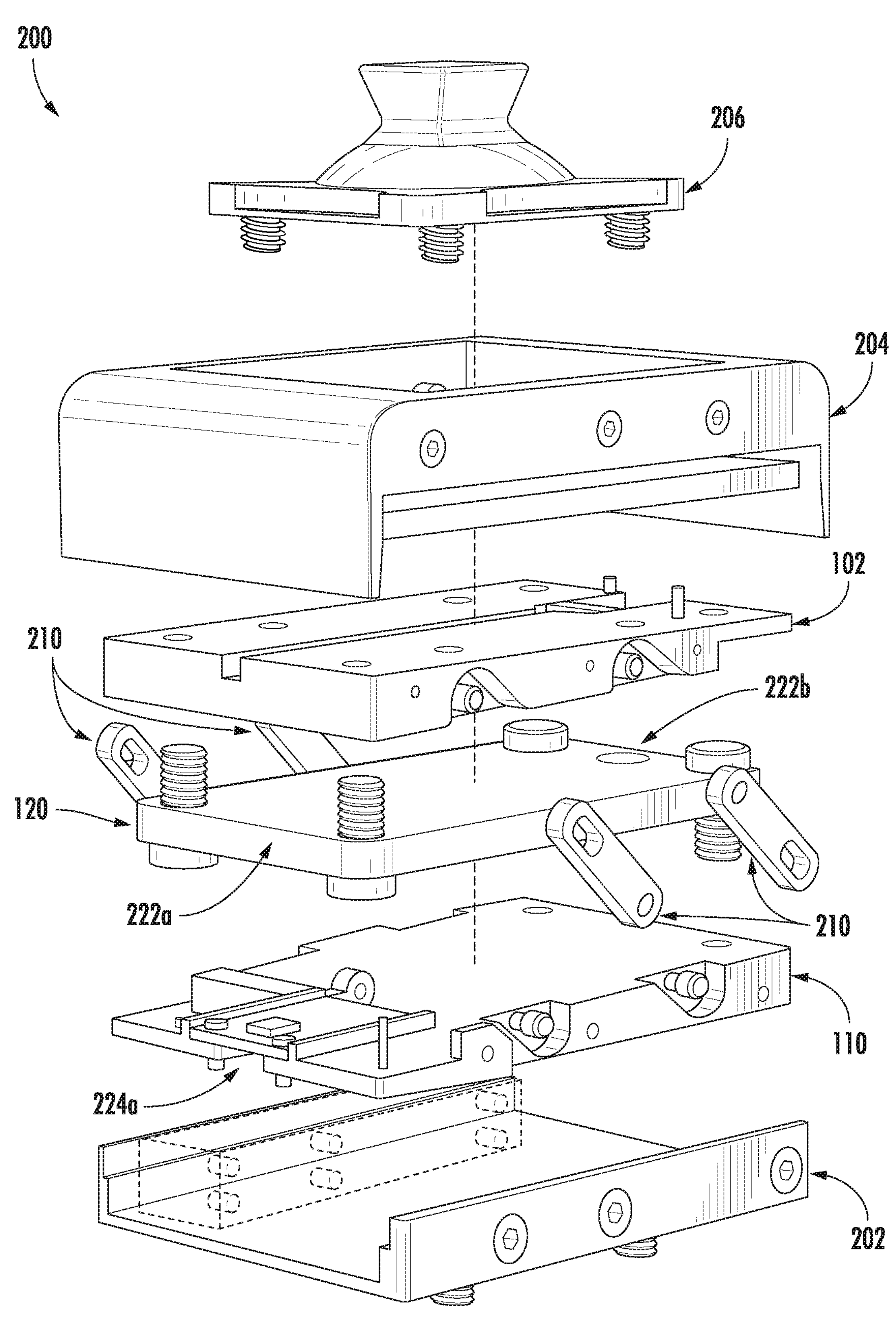
FIG. 2A illustrates an exploded view of a force-moment sensor configured for use in a powered prosthetic, according to an example implementation of the present disclosure.

Referring now to FIGS. 2A-2D, a force-moment sensor 200 is shown including the first block 102 and the second block 110 described with reference to FIGS. 1A-C. With reference to FIG. 2A, an exploded view of a force-moment sensor 200 is shown, according to an implementation of the present disclosure.

The force-moment sensor 200 includes a mounting surface 202 and a housing 204 that can enclose part of the sensor (e.g. first and second blocks 102, 110). The housing 204 can be a 3D-printed cover in some implementations. The housing 204 can be added to encapsulate part or all of the sensor and protect some or all of the interior components (e.g. first and second blocks 102, 110).

Additionally, the mounting surface 202 and housing 204 can be configured to attach to a prosthesis The mounting surface 202 can be on either the top or bottom of the sensor. Optionally, the mounting surface 202 can include a detachable adapter to allow the sensor 200 to be mounted to a lower-limb prosthesis using the threaded holes for the standard pyramid connector (i.e., mounting the adapter to the prosthesis using the threaded holes, and then attaching the rest of the FM-PLS to the adapter). As such, the implementations of the force-moment sensor 200 can be integrated into the prosthesis structure without affecting the standard connection interface, essentially forming a sensorized pyramid connector [12].

As shown in FIG. 2A, the housing 204 can be configured to attach to a pyramidal adapter 206 that can connect to a prosthesis. It should be understood that the pyramidal adapter 206 is a non-limiting example, and that the sensor can be attached using any kind of attachments (screws, bolts, adhesives, etc.). Alternatively or additionally, the housing 204 and/or mounting surface 202 can be mounted to different types of adapters (i.e., adapters other than pyramidal adapters).

Additionally, the present disclosure contemplates that the force-moment sensor can be installed on/in different parts of a prosthesis. For example, the force moment sensor 200 shown in FIG. 2A-2D can be installed above or below a powered joint of a powered prosthesis. As used herein, the term "powered prosthesis" includes any prosthesis that includes a powered actuator. A non-limiting example actuator is a motor, and it should be understood that powered actuators can be part of prosthetic joints such as knees, ankles, wrists, elbows, and shoulders. When the force-moment sensor is installed near a powered joint of a powered prosthesis, the mounting surface 202 can be connected to the powered joint, and the pyramidal adapter 206 can be configured to connect to a section of a prosthesis.

As shown in FIG. 2A, the force-moment sensor 200 can include bars 210 that can join the first block 102 and the second block 110. The bars 210 can keep the first block 102 and second block 110 close together, and restrict the motion of the first block 102 relative to the second block 110. The bars 210 can prevent the sensor from pulling too far apart when subjected to pulling forces (i.e., forces that pull the first block 102 away from the second block 110.

The bars 210 can be added on each side of the sensor 200 to limit the extension when a pulling force is applied (e.g., during the swing of a prosthesis). For example, in FIG. 2A, a pair of bars 210 is provided on opposite sides of the sensor 200. It should be understood that the number and arrangement of the bars 210 shown in FIG. 2A is provided only as an example. This disclosure contemplates using a different number and/or arrangement of bars.

The implementation of the present disclosure shown in FIG. 2A uses two magnetic sensors to measure the deflection of the elastic element 120. In the implementation shown in FIG. 2A, the elastic element 120 includes a first magnet 222*a* and a second magnet 222*b*, each arranged at an opposite end of the elastic element 120. The first magnet 222*a* and the second magnet 222*b* move relative to the first block 102 and second block 110 as force is applied to one or both blocks. The first block 102*a* has a first magnetic sensor (not shown) and the second block 110 has a second magnetic sensor 224*a*. So the magnetic sensor 224*a* can detect the movement of the magnets 222*a*, 222*b* relative to the first block 102 and the second block 110, and thereby measure the deflection of the elastic element 120.

Figure 2B:
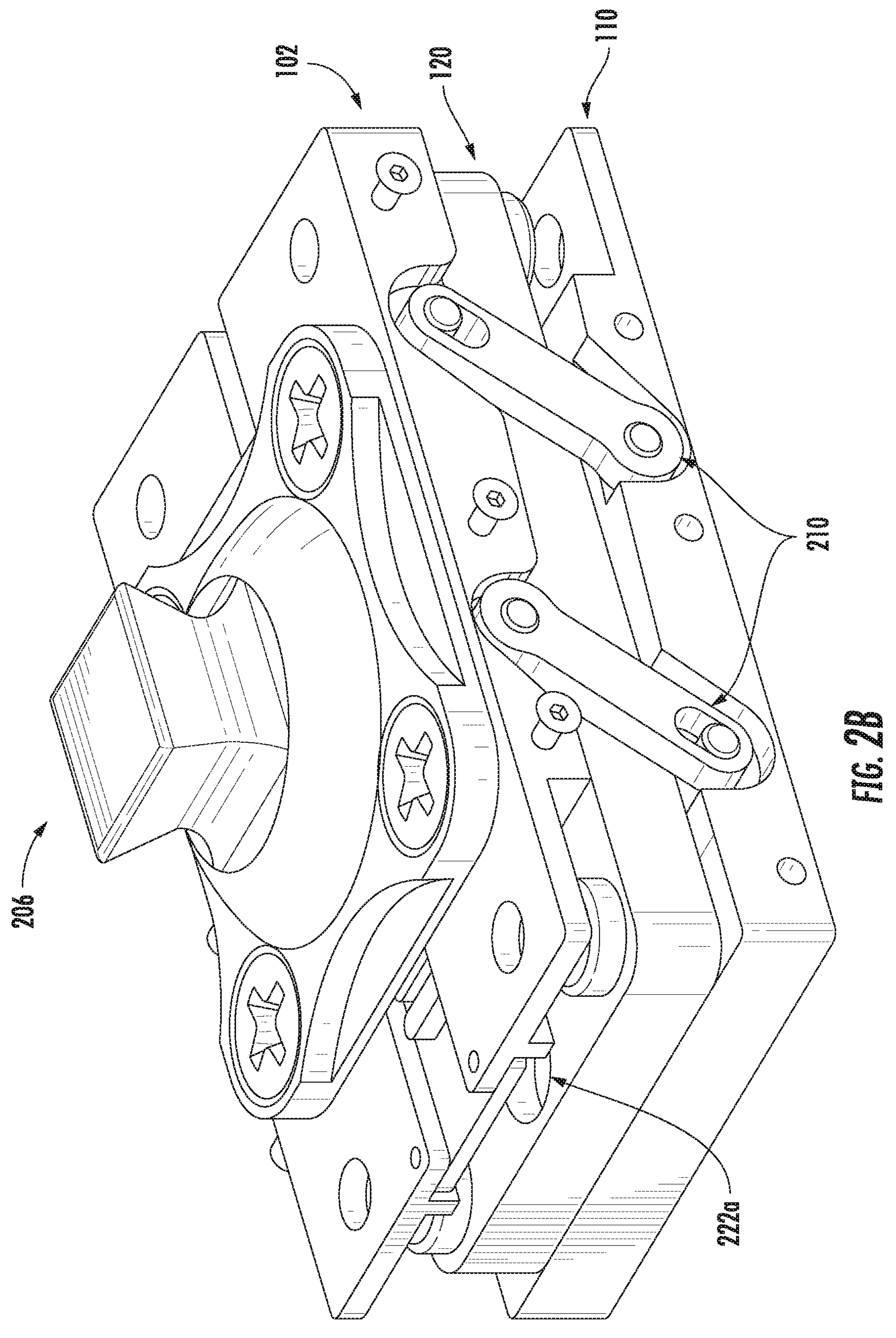
FIG. 2B illustrates a perspective view of the force-moment sensor illustrated in FIG. 2A without a housing.

FIG. 2B illustrates a perspective view of the force-moment sensor 200 shown in FIG. 2A. In turn, FIG. 2C illustrates a side view of the force-moment sensor 200 shown in FIG. 2B.

Figure 2C:
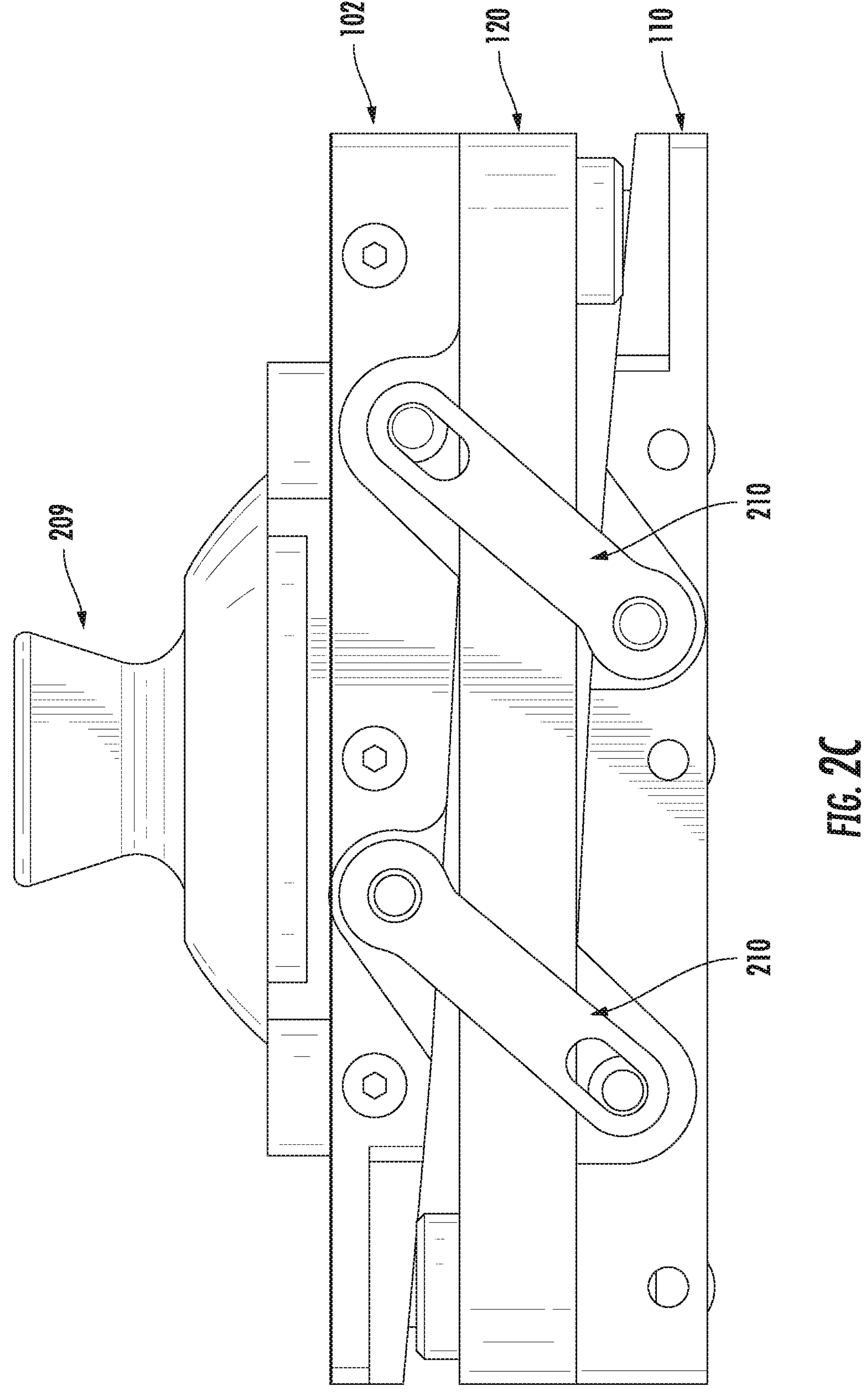
FIG. 2C illustrates a side view of the force-moment sensor illustrated in FIG. 2A.
Figure 2D:
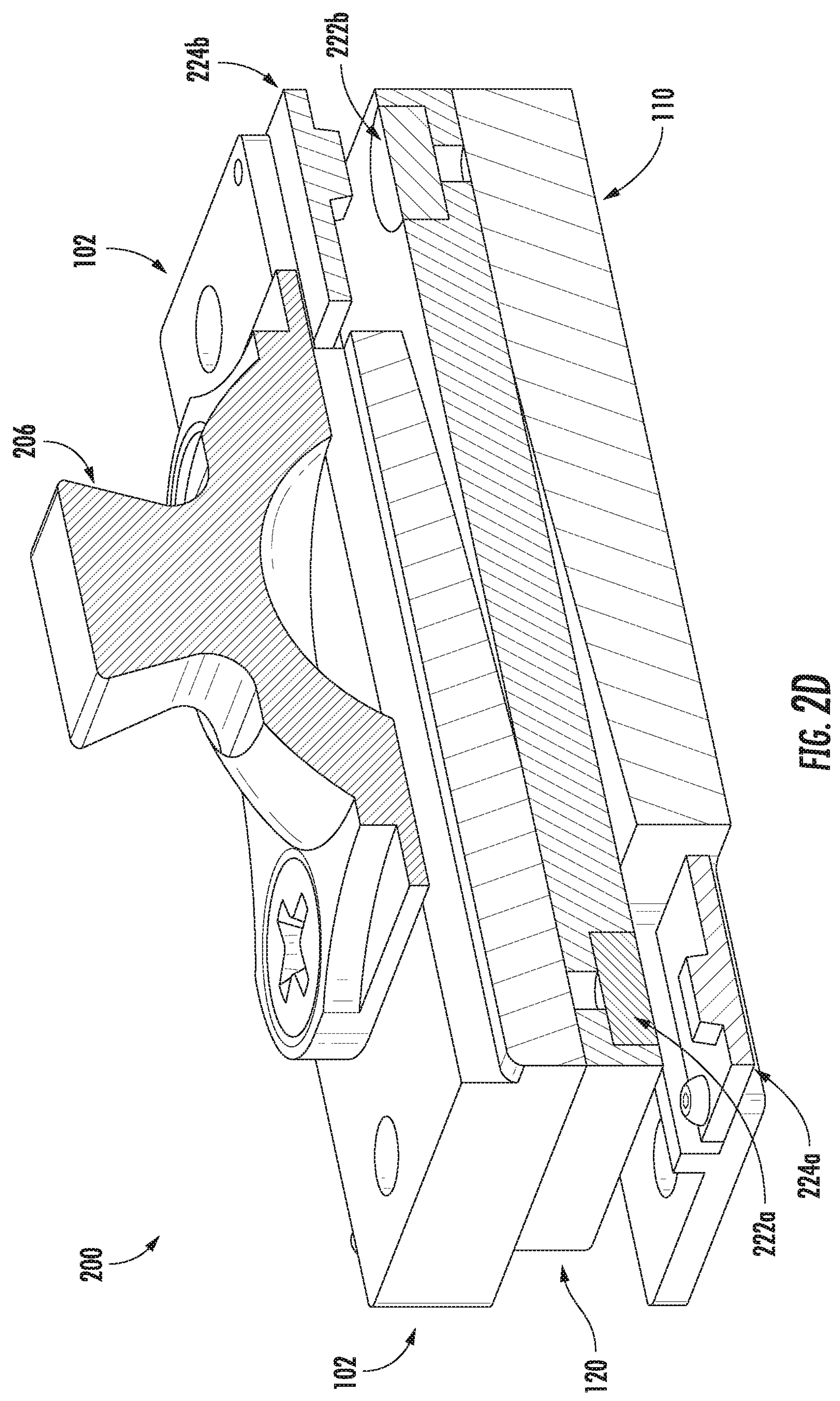
Figure 2D:
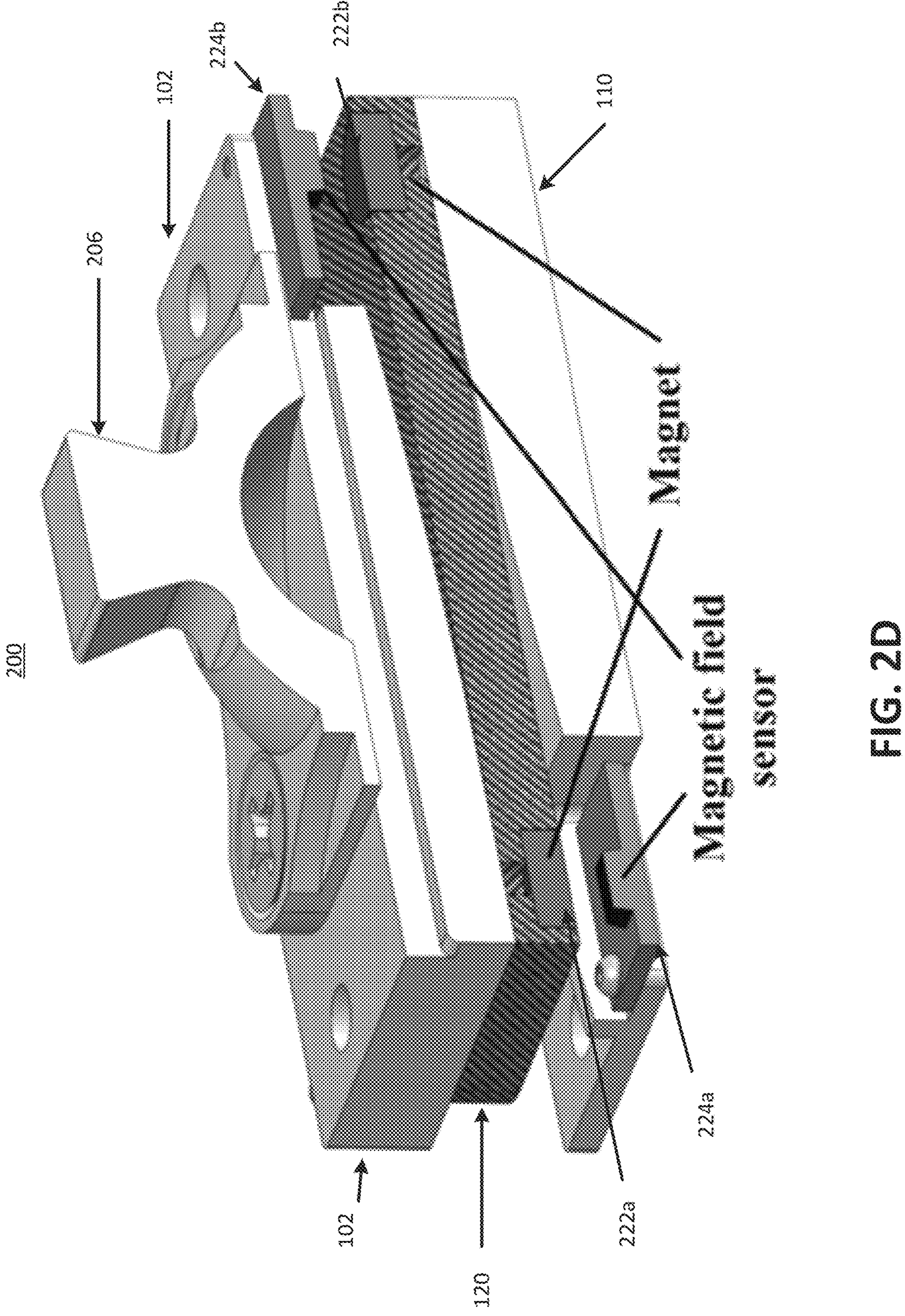

FIG. 2D illustrates a cross sectional view of the force-moment sensor 200 shown in FIGS. 2A-2C. The force-moment sensor 200 includes the first magnet 222*a* and second magnet 222*b* in the elastic element 120. Two magnetic sensors 224*a* 224*b* are shown in the cross sections of the first block 102 and second block 110. As the blocks 102 110 move relative to the elastic element 120, the distance between the magnets 222*a* 222*b* and the respective magnetic sensors 224*a* 224*b* changes, which can allow for measurements of both axial force and bending moment, as described throughout the present disclosure. Optionally, the magnetic sensors 224*a* 224*b* can be magnetic encoders in some implementations of the present disclosure.

Figure 3A:
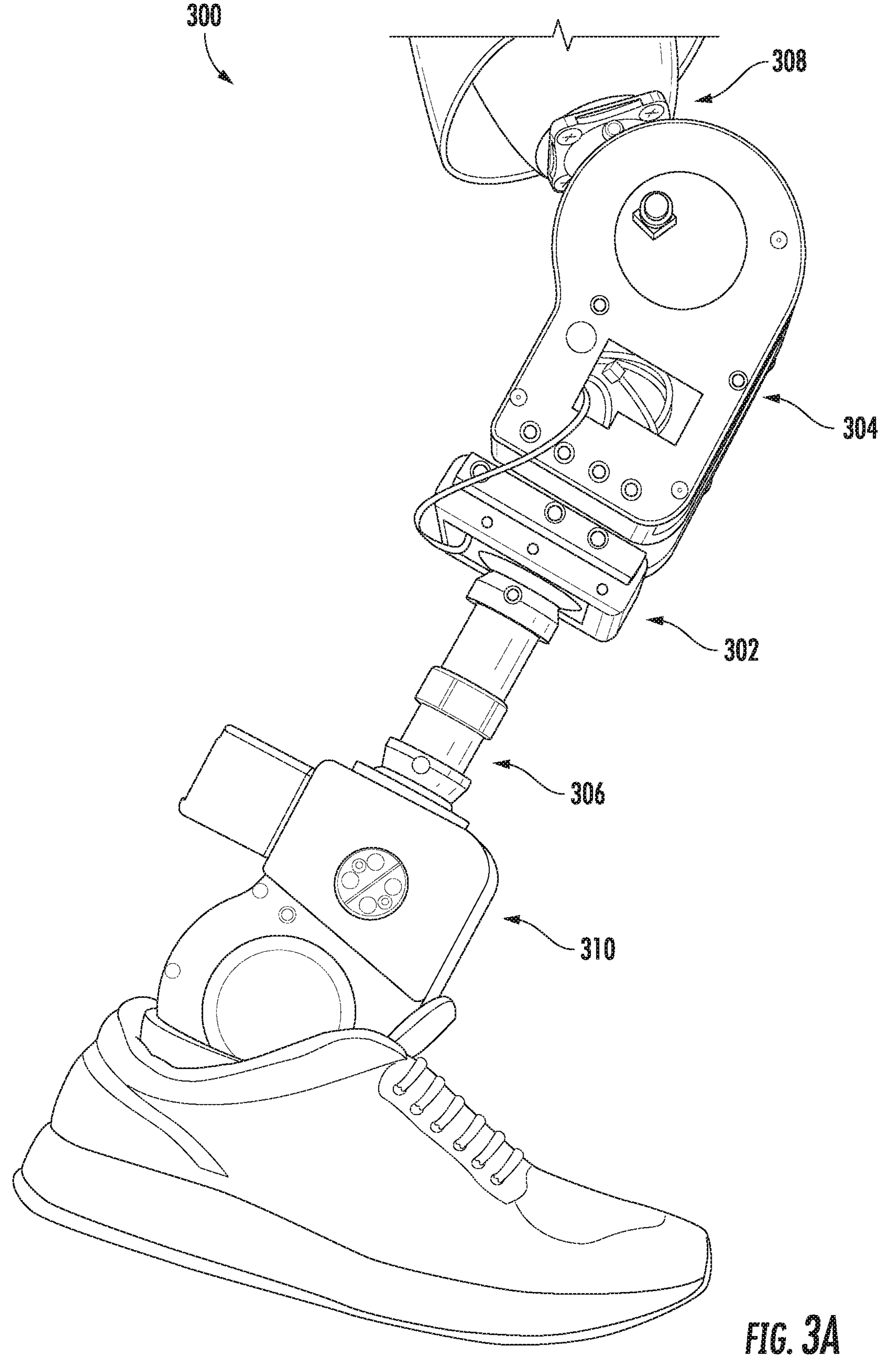
FIG. 3A illustrates a powered prosthetic leg including a force-moment sensor, according to an example implementation of the present disclosure.

An example implementation of the present disclosure was tested. FIG. 3A illustrates a powered prosthetic leg 300 including a force-moment sensor 302. This disclosure contemplates that the force-moment sensor 302 can be the force-moment sensor described above with regard to FIGS. 1A-1B or FIGS. 2A-2C. The force-moment sensor 302 is connected to the powered prosthetic knee 304, and also connected to the lower leg section 306.

It should be understood that in some implementations the force-moment sensor 302 could be connected between the powered prosthetic knee 304 and the upper leg section 308, or between the powered prosthetic ankle 310 and the lower leg section 306. Additionally, it should be understood that the prosthetic knee is intended only as a non-limiting example of a prosthetic where the force-moment sensor 302 can be applied. Implementations of the present disclosure can be used in any prosthetic, including prosthetic arms (including any or all of elbow, wrist, and shoulder joints), any prosthetic legs (including ankle and hip joints). Moreover, it should be understood that the force-moment sensors described herein can be positioned in/on the prosthetic in locations other than the joint, e.g., at some part of the prosthetic leg, arm, hand, or foot.

Implementations of the present disclosure can be used to acquire data that can be used to control powered prostheses (e.g., the powered prosthetic leg 300 shown in FIG. 3A). The force moment sensors described herein can be part of a system including any number of powered prostheses. The system can include one or more computing devices (e.g., the computing device 400 shown in FIG. 4). The computing devices can receive the output of the one or more sensors and use the sensor output to determine the amount of deflection of the elastic element inside the sensor. The relationship between the amount of deflection and the amount of force on the elastic element can be used to determine the amount of force on the elastic element based on the deflection. Additionally, the relationship between the force on the elastic element and the force on the sensor or on the prosthesis can also be determined by the computing devices.

In addition to determining the force on the elastic element and/or the force on the sensor or prosthesis, the computing device 400 can control the motor in a powered prosthesis. The control of the motor can be based on the forces determined by the computing device 400. For example, the computing device 400 can determine that the prosthetic is contacting something, or not contacting something, based on the measured forces. In implementations where the prosthetic is a prosthetic leg, the computing device 400 can determine when the leg is touching the ground, when the user is placing weight on the prosthesis, and how to move motors in the powered prosthesis to move the user in a walking motion.

Because the deflection of the elastic element can be correlated to the forces on the prosthesis, the deflection of the elastic element can be used as an input to the controller for the powered prosthesis. For example, forces on the prosthesis can indicate that the prosthesis is in contact with something (e.g., the ground) and how much weight is being placed on the prosthesis. In a powered prosthetic leg, the forces on the prosthesis can be used to determine when the prosthetic foot is touching the ground and then control powered joint(s) of the powered prosthetic leg to execute a walking motion based on when the leg is (and is not) touching the ground.

Additionally, the computing device can be configured to distinguish between a force and a moment of force applied to the force-moment sensor based on the signal or signals received from the sensor(s).

The present methods and systems may be understood more readily by reference to the following detailed description of preferred embodiments and the Examples included therein and to the Figures and their previous and following description.

Example Computing Device

It should be appreciated that the logical operations described herein with respect to the various figures may be implemented (1) as a sequence of computer implemented acts or program modules (i.e., software) running on a computing device (e.g., the computing device described in FIG. 4), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 4:
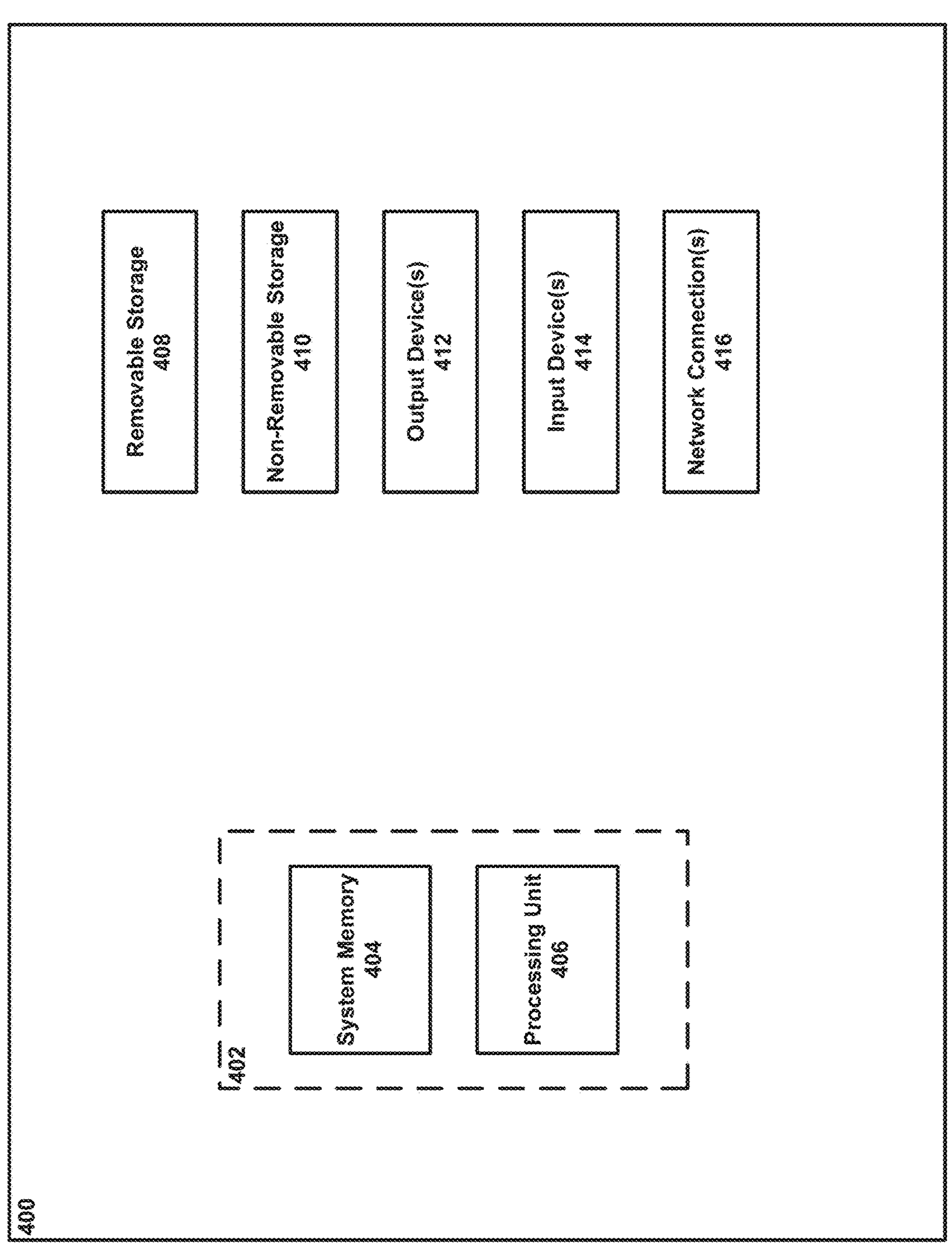
FIG. 4 is an example computing device.

Referring to FIG. 4, an example computing device 400 upon which the methods described herein may be implemented is illustrated. It should be understood that the example computing device 400 is only one example of a suitable computing environment upon which the methods described herein may be implemented. Optionally, the computing device 400 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 400 typically includes at least one processing unit 406 and system memory 404. Depending on the exact configuration and type of computing device, system memory 404 may be volatile (such as random access memory (RAM)), non-volatile (such as read-only memory (ROM), flash memory, etc.), or some combination of the two. This most basic configuration is illustrated in FIG. 4 by dashed line 402. The processing unit 406 may be a standard programmable processor that performs arithmetic and logic operations necessary for operation of the computing device 400. The computing device 400 may also include a bus or other communication mechanism for communicating information among various components of the computing device 400.

Computing device 400 may have additional features/functionality. For example, computing device 400 may include additional storage such as removable storage 408 and non-removable storage 410 including, but not limited to, magnetic or optical disks or tapes. Computing device 400 may also contain network connection(s) 416 that allow the device to communicate with other devices. Computing device 400 may also have input device(s) 414 such as a keyboard, mouse, touch screen, etc. Output device(s) 412 such as a display, speakers, printer, etc. may also be included. The additional devices may be connected to the bus in order to facilitate communication of data among the components of the computing device 400. All these devices are well known in the art and need not be discussed at length here.

The processing unit 406 may be configured to execute program code encoded in tangible, computer-readable media. Tangible, computer-readable media refers to any media that is capable of providing data that causes the computing device 400 (i.e., a machine) to operate in a particular fashion. Various computer-readable media may be utilized to provide instructions to the processing unit 406 for execution. Example tangible, computer-readable media may include, but is not limited to, volatile media, non-volatile media, removable media and non-removable media implemented in any method or technology for storage of information such as computer readable instructions, data structures, program modules or other data. System memory 404, removable storage 408, and non-removable storage 410 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 406 may execute program code stored in the system memory 404. For example, the bus may carry data to the system memory 404, from which the processing unit 406 receives and executes instructions. The data received by the system memory 404 may optionally be stored on the removable storage 408 or the non-removable storage 410 before or after execution by the processing unit 406.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Example Embodiment

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Human walking is a cyclic movement that involves coordinated reciprocating motion of two legs. Despite the continuous forward motion of the upper body, each leg's motion pattern can be essentially discrete, with vastly different dynamic behaviors across different phases in a single gait cycle [1]. During the swing phase, the leg joints (especially the knee) display low impedance, generating a pendulum-like swing motion to reposition the leg in front of the upper body to prepare for the next heel strike. During the stance phase, the leg joints display much elevated impedance, preventing the leg from buckling under the load imposed by the body weight. For individuals living with lower limb losses, restoring the locomotive functions require their prosthetic devices to replicate the dynamics characteristics of the biological legs, especially the significant differences between the stance and swing phases.

With the technological advances in actuation, electronics, and control, micro-processor-controlled (MPC) knee prostheses were developed [2, 3]. MPC prostheses regulate joint resistance during different gait phases with hydraulic or pneumatic circuits, and some also provide swing assistance using mechanical springs [4]. Realizing such functionality obviously require accurate and reliable detection of gait phase in real-time, which is usually conducted through the measurement of prosthesis structural load (e.g., using a sensorized pylon in the C-Leg). The prosthesis structural load can be a useful parameter to measure for the determination of the gait phase, but also for the quantification of the prosthetic leg load bearing for more sophisticated functions (e.g., to trigger the sit-to-stand assistance when an amputee shifts load to his/her leg prosthesis [5]).

For load measurement, strain measurement can be used. Strain gauges can be firmly attached to the load-bearing structure to measure the underlying micro-scale deflection, which correlates to the magnitude to the applied load [6-7]. Strain gauges can be attached to structural components (e.g., pylons), or a dedicated structure can be designed and instrumented to form a force sensor (i.e., load cell). For example, a 3-axis socket load cell adapted to a leg where regions of compression and tension were clearly defined in a double-cross structure for strain measurement [8]. The weak signals generated by strain gauges can be susceptible to interferences, and signal drift may also occur and affect the consistency of the measurement. An alternative approach is the force-sensing resistor (FSR)-based load sensing. FSRs can be placed under the prosthetic feet [9, 10] or embedded in the prosthesis structure for load sensing, but due to their unsatisfactory measurement accuracy and consistency, FSR signals' use has largely been limited to the detection of gait events (e.g., heel strike) for phase transition.

Large structural deformation-based prosthesis load sensing can also be used. Instead of using strain gauges to measure micro-scale deflection, this sensing approach is based on the measurement of much larger (typically millimeter-scale) deformation of load-bearing structures. A non-limiting example is the instrumented pyramid adapter [12], which incorporates a cantilever beam-type structure as the load-sensing element. By using two magnetic sensors to measure the displacements of the two ends of the cantilever beam, this sensor is able to provide robust sensing of the axial force and bending moment in the sagittal plane. However, the cantilever beam structure needs to be accurately machined with high-performance metal (titanium in the prototype), resulting in a high cost of manufacturing. Another example is the parallelogram load cell [13], which also provides reliable load measurement through a parallelogram-configured deformable structure. This load cell may be configured to measure the axial force (not the bending moment), and it is relatively heavy due to the use of a coil spring as the elastic element.

An example embodiment of the present disclosure was designed and fabricated. The example embodiment is referred to herein as the Force-Moment Prosthesis Load Sensor (FM-PLS), and provides reliable measurement of the axial force and bending moment in a lower-limb prosthesis with a simple, lightweight, and inexpensive sensor package. Compared with the strain gauge-based load sensors, the FM-PLS can provide stronger signals, that can be more robust against interference. Compared with the recent large structural deformation-based sensors, the FM-PLS is mechanically simpler and less expensive to manufacture. Thus, the FM-PLS may become a highly useful component for the MPC and robotic (powered) lower-limb prosthesis to make them more reliable, functional, and affordable for the amputee users.

Measurement of prosthesis structural load can be important to quantify the interaction of the amputee user with the environment, can be used for control of smart prosthetic devices. However, the existing force sensors used in prostheses include off-the-shelf loadcells based on strain measurement (using strain gauges) and thus may suffer from issues such as weak signals and signal drift. These off-the-shelf load cells may not be prosthesis compatible, and thus require complex design customization which has a common impact on the size, weight, and usability of the prosthesis.

A study was performed of an example implementation directed to overcoming these and other limitations. The example implementation includes Force-Moment Prosthesis Load Sensor (FM-PLS) to measure the axial force and bending moment in a lower-limb prosthesis structure compatible with the standard pyramid adapter) without modification of the prosthesis. Unlike strain gauges loadcell, the FM-PLS is based on the magnetic sensing of small (millimeter-scale) deflection of an elastic element, which provides stronger signals and is more robust against interferences and drifting. The design of the sensor adopted curved supporting surfaces to modulate the sensitivity such that the measurement is sensitive at light load but still withstand heavy load without damage. To validate the prosthesis performance benchtop testing along with prosthesis walking testing were conducted. The robotic leg prosthesis walking testing of the sensor shows that the sensor signals can be used to detect important gaits events such as ground contact after leg swing and toe-off after the stance phase, facilitating the intelligent motion control of lower-limb prostheses.

Human walking can be modeled as a cyclic movement that involves coordinated reciprocating motion of two legs. Despite the continuous forward motion of the upper body, each leg's motion pattern can be essentially discrete, with different dynamic behaviors across different phases in a single gait cycle [1]. During the swing phase, the leg joints (especially the knee) display low impedance, generating a pendulum-like swing motion to reposition the leg in front of the upper body to prepare for the next heel strike. During the stance phase, the leg joints display much elevated impedance, preventing the leg from buckling under the load imposed by the body weight. For individuals living with lower limb losses, restoring the locomotive functions can require their prosthetic devices to replicate the dynamic characteristics of the biological legs, especially the significant differences between the stance and swing phases.

Leg prostheses can be simple, purely mechanical devices with very limited capability of regulating joint behavior. With the technological advances in actuation, electronics, and control, micro-processor-controlled (MPC) knee prostheses were developed and entered clinical practice, for example, Ottobock C-Leg [2] and Ossur Rheo Knee [3]. Typical MPC prostheses regulate joint resistance during different gait phases with hydraulic or pneumatic circuits, and some also provide swing assistance using mechanical springs [4]. Realizing such functionality can require accurate and reliable detection of the gait phase in real-time, which is usually conducted through the measurement of prosthesis structural load (e.g., using a sensorized pylon in the C-Leg). More recently, powered robotic lower-limb prostheses started to emerge, include the Vanderbilt Leg, MIT ankle-foot prostheses, and Ossur PowerKnee. With their capability of providing actively powered joint action, the importance of prosthesis structural load is further highlighted, not only for the determination of the gait phase, but also for the quantification of the prosthetic leg load bearing for more sophisticated functions (e.g., to trigger the sit-to-stand assistance when an amputee shifts load to his/her leg prosthesis [5])

For load measurement, the most extensively used method is strain measurement. Strain gauges can be firmly attached to the load-bearing structure to measure the underlying micro-scale deflection, which correlates to the magnitude to the applied load [6]. Strain gauge-based load measurement has been applied to the orthopedics since 1970s [7], and it still remains as a major approach for the prosthesis structural load measurement. Strain gauges can be attached to structural components (e.g., pylons), or a dedicated structure can be designed and instrumented to form a force sensor (i.e., load cell). For example, Sup et al. developed a 3-axis socket load cell for the control of an early version of Vanderbilt Leg, in which regions of compression and tension were defined in a double-cross structure for strain measurement [8]. Despite the maturity of such a technique, the weak signals generated by strain gauges are susceptible to interferences, and signal drift may also occur and affect the consistency of the measurement. An alternative approach, similar to the strain gauge method, is the force-sensing resistor (FSR)-based load sensing. FSRs can be placed under the prosthetic feet [9,10] or embedded in the prosthesis structure for load sensing, but due to their unsatisfactory measurement accuracy and consistency, FSR signals' use has largely been limited to the detection of gait events (e.g., heel strike) for phase transition.

Structural deflection-based prosthesis load sensing can also be used. Instead of using strain gauges to measure micro-scale deflection, this new sensing approach is based on the measurement of much larger (typically millimeter-scale) deflection of load-bearing structures. An example is the instrumented pyramid adapter developed by Gabert and Lenzi [12], which incorporates a cantilever beam-type structure as the load-sensing element. By using two magnetic sensors to measure the displacements of the two ends of the cantilever beam, this new sensor is able to provide robust sensing of the axial force and bending moment in the sagittal plane. However, the cantilever beam structure needs to be accurately machined with high-performance metal (titanium in the prototype), resulting in high cost of manufacturing. Another example is the parallelogram load cell developed for the Vanderbilt Leg [13], which also provides reliable load measurement through a parallelogram-configured deformable structure. As its major weaknesses, this load cell only measures the axial force (not the bending moment), and it is relatively heavy due to the use of a coil spring as the elastic element.

The example implementation studied in the present example includes a prosthesis load sensor referred to herein as the Force-Moment Prosthesis Load Sensor (FM-PLS). The FM-PLS provides reliable measurement of the axial force and bending moment in a lower-limb prosthesis with a simple, lightweight, and inexpensive sensor package. Compared with the strain gauge-based load sensors, the FM-PLS provides stronger signals, more robust against interferences. Compared with structural deflection-based sensors, the FM-PLS is mechanically simpler and less expensive to manufacture.

The study described herein includes the development of this FM-PLS sensor along with the related results obtained through finite-element analysis and experimental testing. The study included FM-PLS design and development, including sensing principle and the electronic components: experimental procedure; and the results to validate the performance of the FM-PLS.

The functioning mechanism of the FM-PLS can be based on two-stage transduction: (1) Displacement due the deformation of elastic element by applied force or bending moment, and (2) Magnetic field transduction due to change in distance between the magnet and magnetic field transducer.

In the 1st stage transduction, a flat carbon fiber or fiberglass piece, serves as the elastic element 120 (shown in FIG. 1A) to deform under load. Each end of this elastic element 120 is rigidly attached to a curved mounting block in a cantilever beam-like configuration, as shown in FIGS. 1A-1C. Under an axial force (shown in FIG. 1B), the left and right ends experience symmetric deflections (i.e., $\Delta x_1=\Delta x_2$); under a bending moment, the left and right ends experience asymmetric deflections (i.e., $\Delta x_1 \neq \Delta x_2$) (FIG. 1C). As such, any combination of the axial force and bending moment can be measured by independently measuring the small deflections at the left and right ends ($\Delta x_1$ and $\Delta x_2$).

The deflection of the elastic element 120 changes the relative distance between the magnets (not shown) and the magnetic field sensors located on top/bottom of the magnets. Since the magnetic flux density is a function of distance from the magnet, magnetic flux density measured by the magnetic field transducers (not shown) changes due to the change of distance by applying force. The output of the magnetic field transducer is voltage. Thus, the applied force is sensed as the voltage by the transducer through two-stage transductions.

Both stages of the transduction principle can have an impact on its capacity to measure force and bending moment. To establish the relationship between applied force and magnetic field sensor voltage output, analyses (either simulation or mathematical) have been carried out in multiple stages. The elastic element 120 between the upper block (e.g., the first block 102) and lower blocks (e.g., the second block 110) works as a cantilever beam. Hence the deflection of the elastic element 120 is a function of the active length of the cantilever beam. This sensor design adopts a curved surface for both upper and lower blocks (as shown in FIGS. 1A-1C) which modulates the active length of the elastic element 120 and thus controls the deflection. That means this feature makes the sensor sensitive at low force while still withstanding heavy load without damage.

Figure 5B:
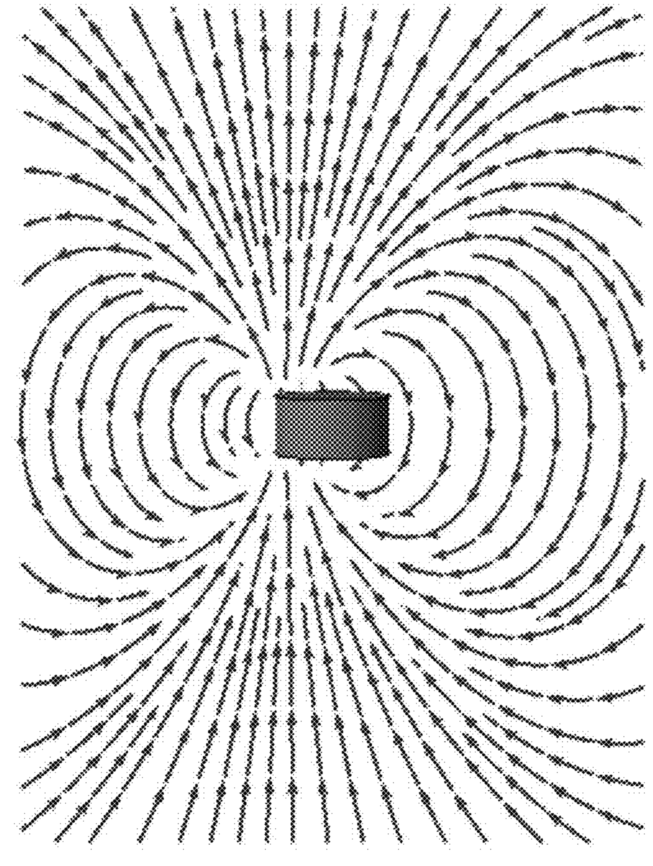
FIG. 5B illustrates an illustration of an example magnetic field that can be formed by the example cylindrical bar magnet of FIG. 5A.
Figure 5A:
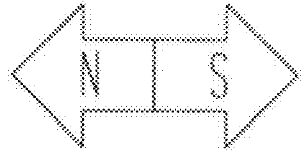
FIG. 5A illustrates an example cylindrical bar magnet that can be used as part of a magnetic sensor in implementations of the present disclosure.
Figure 5A:
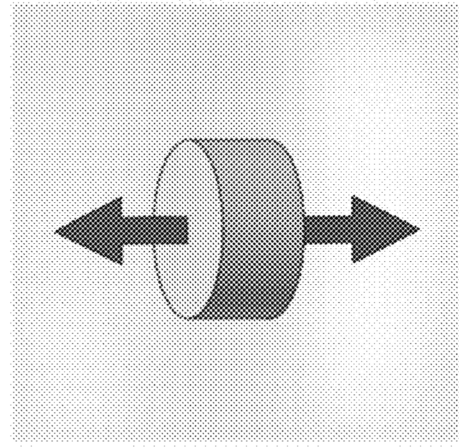
Figure 6:
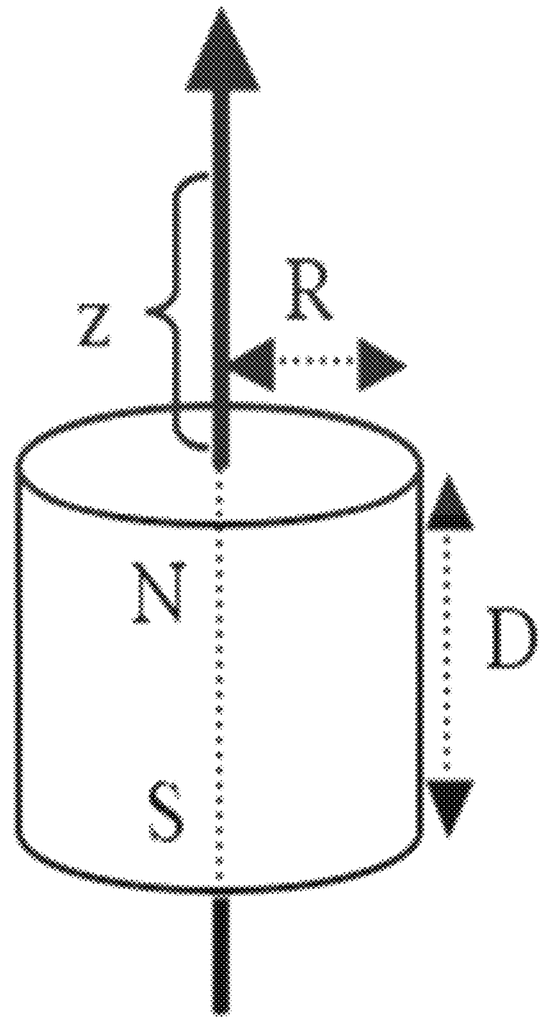
FIG. 6 illustrates the magnetic flux density of a cylindrical bar magnet (radius R and thickness D) in the axial direction at a distance z

The second stage of transduction relies on the amount of the magnetic flux measured by the magnetic field sensor. Although the magnetic field is related to the distance from the magnet, yet the magnetic fields around a magnet are not uniform in all directions. The magnetic field depends on numerous factors, including the shape of the magnet, the distance between the poles, as well as the specific position around the magnet. The magnet used in the sensor design can be considered as the cylindrical bar magnet whose two opposite faces are the two poles. FIG. 5A illustrates a cylindrical bar magnet and FIG. 5B which illustrates a magnetic field surrounding the cylindrical bar magnet. FIG. 6 illustrates the magnetic flux density of a cylindrical bar magnet (radius R and thickness D) in the axial direction at a distance z The magnetic flux density at a distance z (as shown in FIG. 3.), in the axial direction can be expressed as the equation (1) [15], where D is the thickness of the magnet, R is the radius of the magnet and Br is the radial component of the magnetic flux density in the axial direction.

$$B = \frac{B_r}{2}\left(\frac{D+z}{\sqrt{R^2+(D+z)^2}} - \frac{z}{\sqrt{R^2+z^2}}\right) \quad (1)$$

An objective of FM-PLS was to measure the axial force and bending moment simultaneously while minimizing the mechanical complexity.

The example implementation of an FM-PLS can include four main structural components and two sets of sensing components. The structural components can include: (1)

Elastic element 120, (2) Upper mounting block (e.g., the first block 102), (3) Lower mounting block (e.g., the second block 110), and (4) Detachable adapter (e.g., a mounting surface 202 configured to attach to a detachable adapter), as shown in FIG. 2A. The elastic element is the sensor's core structural component which is mounted to the upper and lower block on each end. By measuring the upper and lower blocks' relative displacement (determined by the elastic deflection of the member), the axial force and bending moment can be determined accordingly. The mating surface of the lower/upper block with the elastic member is curved to modulate the deflection of the elastic member.

The sensing components can include a magnetic field sensor and magnet. For the measurement of the deflections, a miniature magnet can be embedded on each end of the elastic element, and a magnetic sensor can be embedded in the free end of each curved surface (e.g., the curved surfaces 104 112 shown in FIGS. 1A-1C), measuring the change of the magnetic field due to the movement of the corresponding magnet. As such, the magnet sensors' signals serve as indirect measurements of the force/moment applied to the sensor.

In some implementations, each magnetic sensor can optionally be embedded in a small printed circuit board (PCB), which can also optionally include a signal conditioning circuit. As such, the output signals of the FM-PLS can be optionally be directly routed to the prosthesis' microcontroller as a plug-n-play component.

Figure 3B:
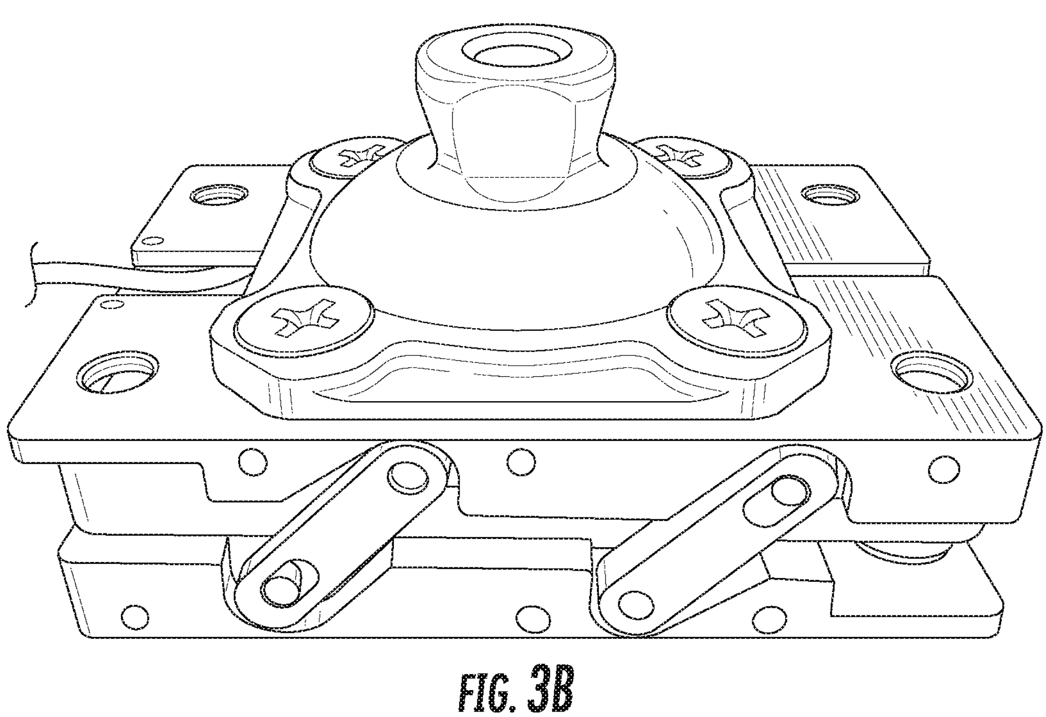
FIG. 3B illustrates a perspective view of an example implementation used in a study of an example implementation.
Figure 3C:
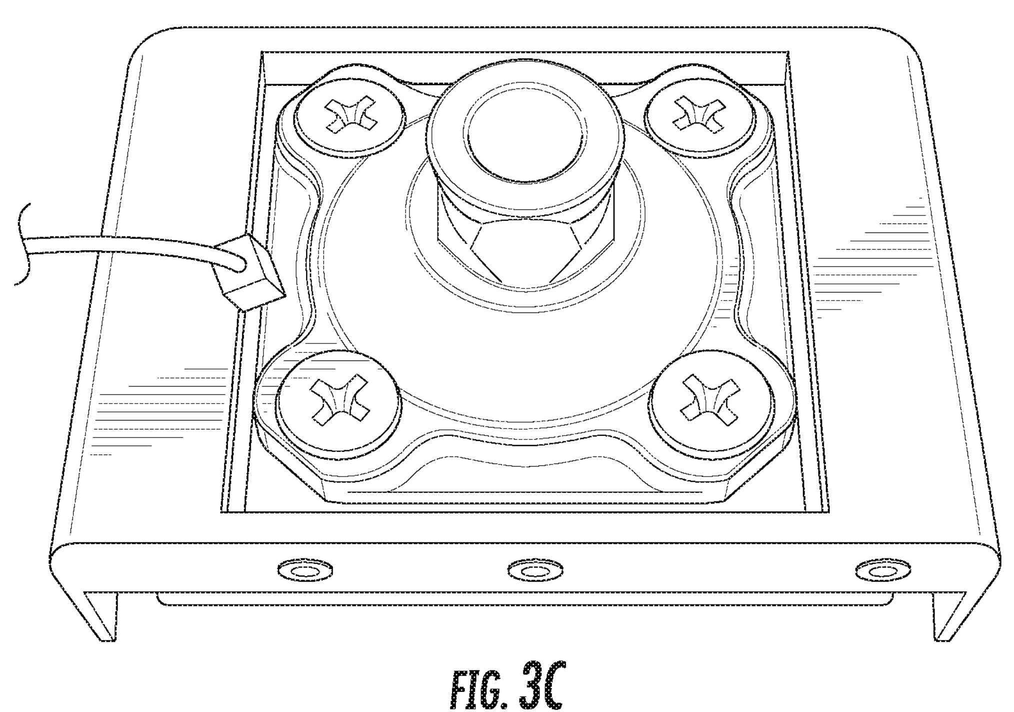
FIG. 3C illustrates a perspective view of the example implementation shown in FIG. 3B.

Further, a pyramid connector (e.g., mounting surface 202 shown in FIG. 2A) can be mounted to the top of the FM-PLS, and a detachable adapter (not shown) can be attached at the bottom of the sensor to allow the sensor to be mounted to a lower-limb prosthesis using the threaded holes for the pyramid connector (e.g., mounting the adapter to the prosthesis using the threaded holes, and then attaching the rest of the FM-PLS to the adapter. As such, the FM-PLS can be easily integrated into the prosthesis structure without affecting the standard connection interface, essentially forming a sensorized pyramid connector (similar to [12]). To facilitate the sensor's practical use in lower-limb prostheses, a pair of slotted bars are added on each side to limit the extension when a pulling force is applied (e.g., during the swing). The elastic member can be made of carbon fiber (e.g., GC-70-UB), while the rest of the structural components were made of 7075 aluminum. Finally, a 3D-printed cover was added to encapsulate the entire sensor and protect the interior components for its future practical use. The prototype of the FM-PLS sensor is show in FIGS. 3A-3C. FIG. 3B illustrates a perspective view of an example implementation used in the study, FIG. 3C illustrates a perspective view of the example implementation shown in FIG. 3B.

Figure 2E:
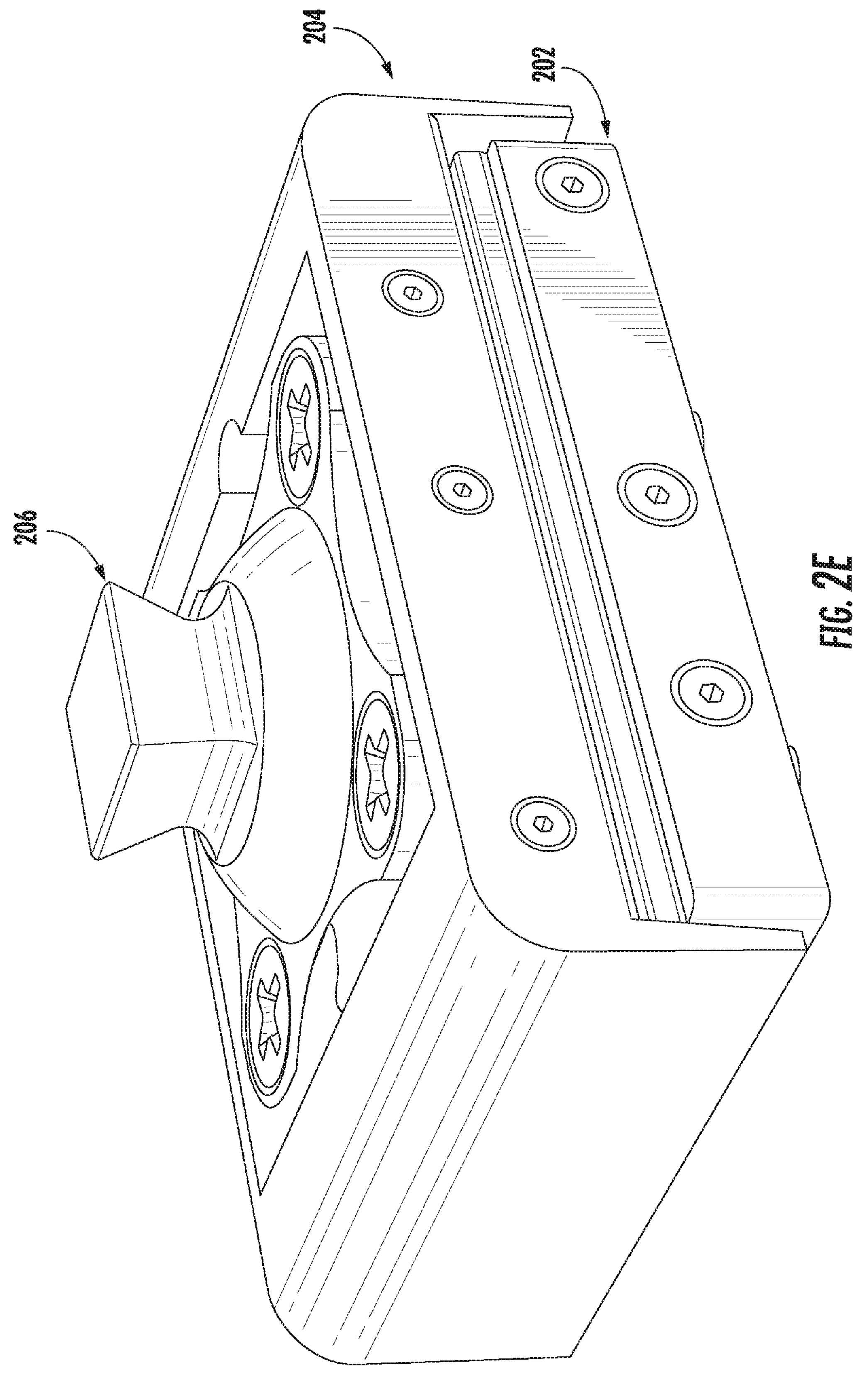
FIG. 2E illustrates a perspective view of the force-movement sensor illustrated in FIG. 2A.
Figure 7A:
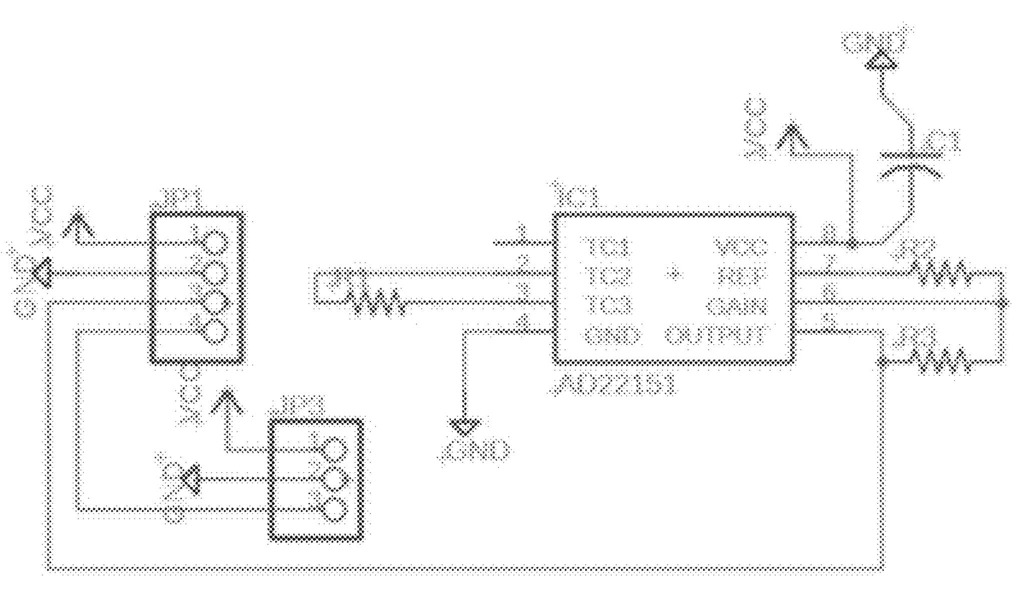
FIG. 7A illustrates an electrical circuit diagram for a magnetic field sensor, according to implementations of the present disclosure.
Figure 7B:
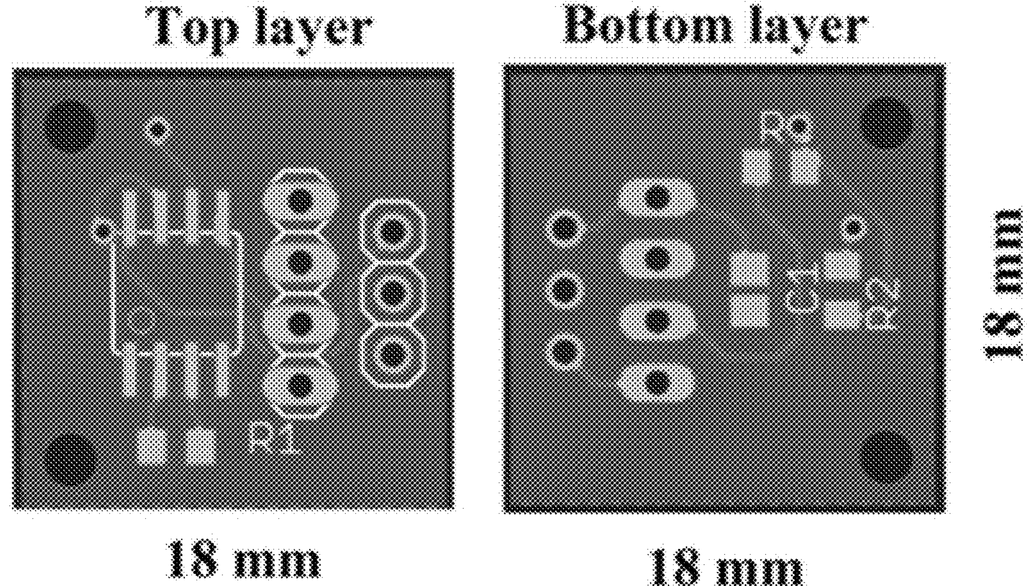
FIG. 7B illustrates an example printed circuit board for a magnetic field sensor, according to implementations of the present disclosure.

As described with reference to FIG. 2D, a custom printed circuit board (PCB) was designed and developed to house the magnetic field sensor along with other electronic components necessary for the force/moment transduction and signal conditioning. A magnetic sensor sold under the trademark AD22151 by Analog Devices, Inc. of Wilmington, Massachusetts was used as the magnetic field sensor. The schematic diagram of the PCB is shown in FIG. 7A. FIG. 7B shows the PCB layout. Two identical small PCBs (18 mm×18 mm) were made for each side of the FM-PLS. The PCBs are mounted on the upper and lower block such that the AD22151 sensors stays on top/bottom of the magnet. Both boards are connected by electrical wires to share the power supply as well as to facilitate the access of both sensor signals from one PCB. The sensor signal can be read in real-time using Analog-to-Digital (ADC) interface. FIG. 2E illustrates a perspective view of the force-movement sensor 200 illustrated in FIG. 2A.

Figure 8:
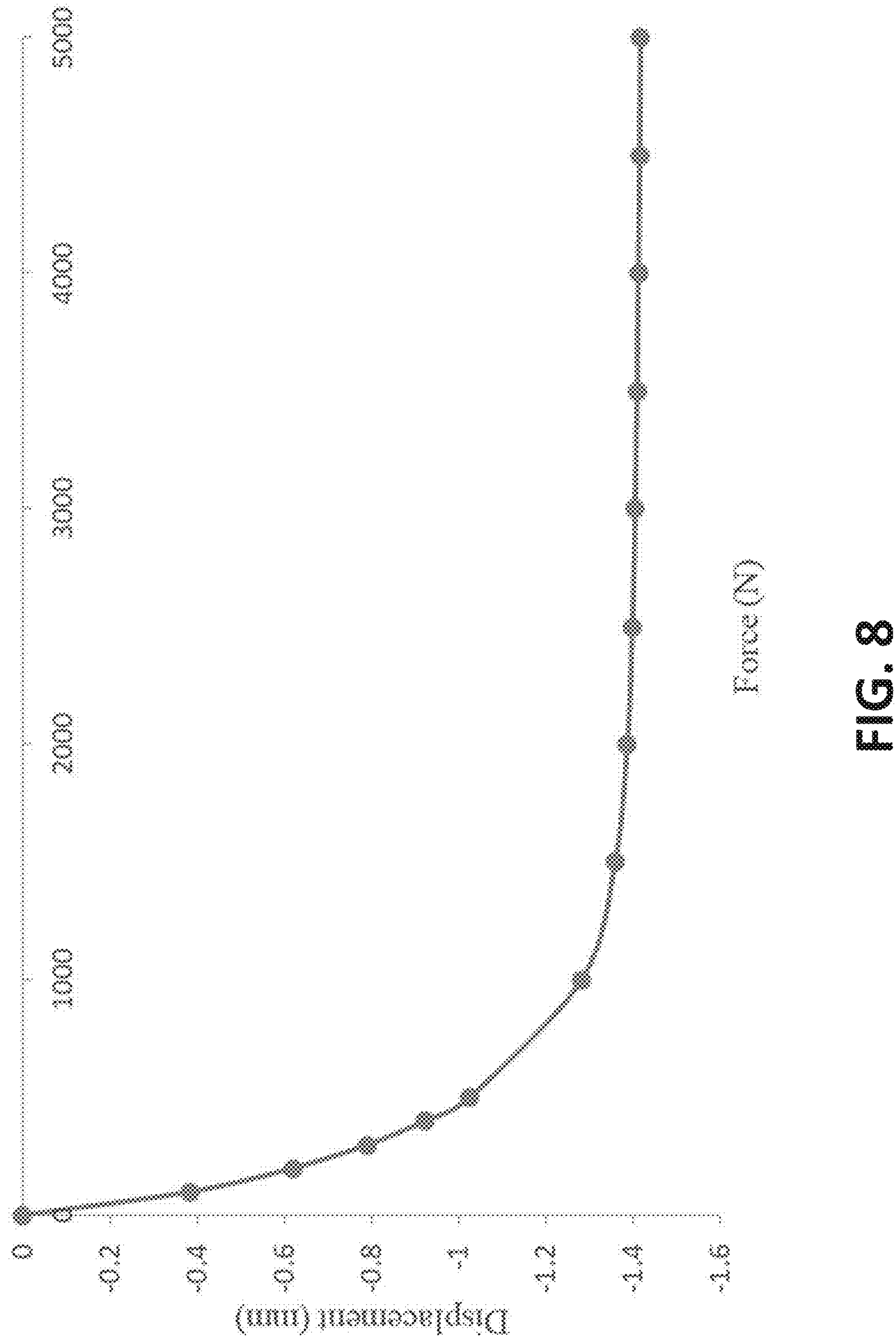
FIG. 8 illustrates a result of a study of the displacement of an example elastic element relative to a magnet while under load, according to implementations of the present disclosure.
Figure 9:
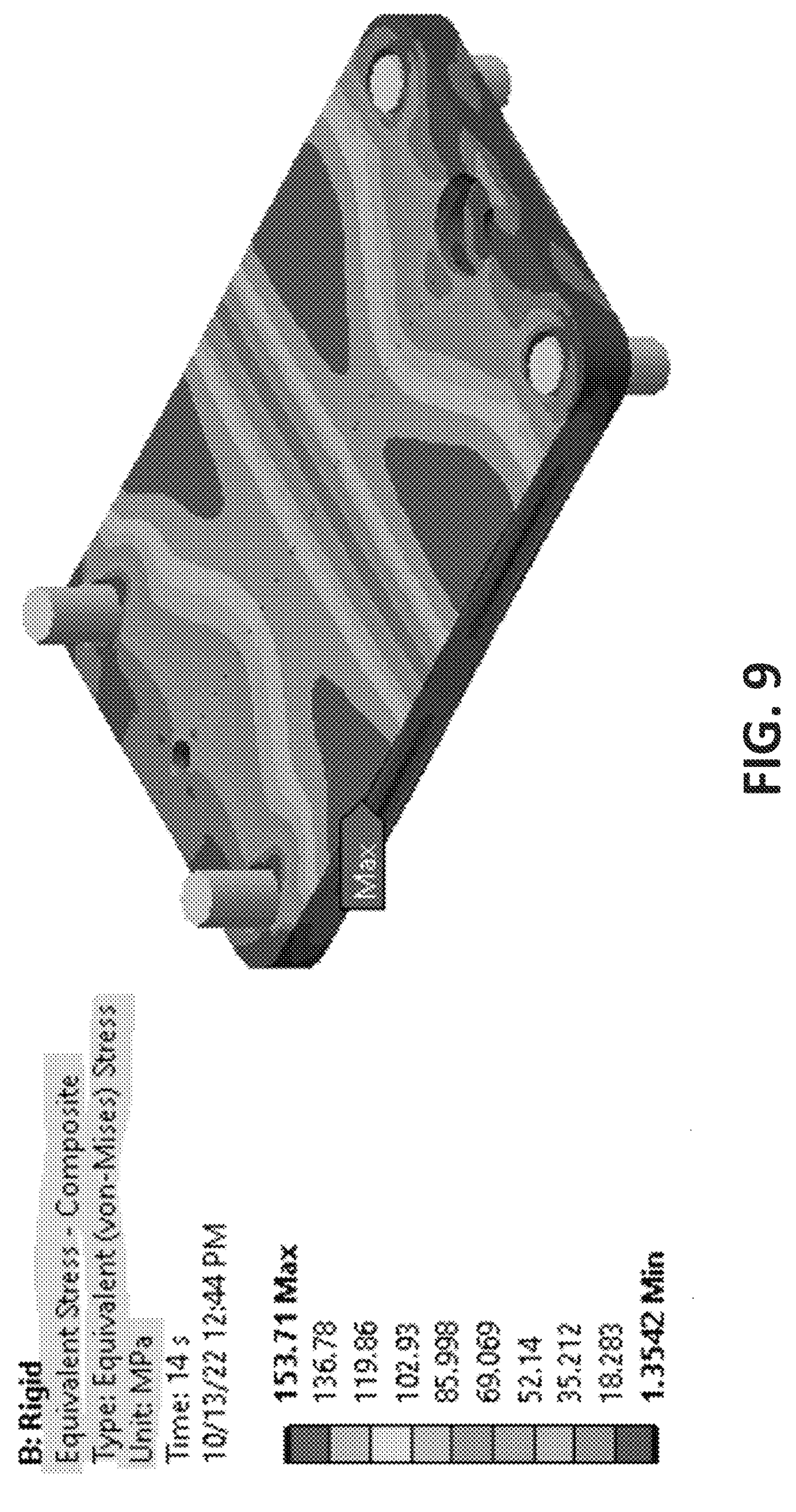
FIG. 9 illustrates a study of stress on an elastic element using a 5000 N axial load, according to implementations of the present disclosure.

The study further included finite element analysis of an example implementation of the present disclosure. To determine the structural displacement, Finite Element Analysis (FEA) was conducted using Ansys (Ansys Inc., Pennsylvania, USA) under various loading conditions. The maximum force was chosen as 5000 N in the analysis which is more than six times of average human adult weight. FIG. 8 shows the displacement of the elastic member at the location of the magnet, by varying the axial force from 0 N to 5000 N. The figure shows that the trend of the displacement is nonlinear as the load increases rather the displacement gradient is decreasing as the load increases. The von mises stress of the FEA is shown in FIG. 9. The maximum stress on the elastic member is 153.71 MPa, which is lower than the tensile strength of the elastic member, meaning it withstands heavy load without damage.

Figure 10:
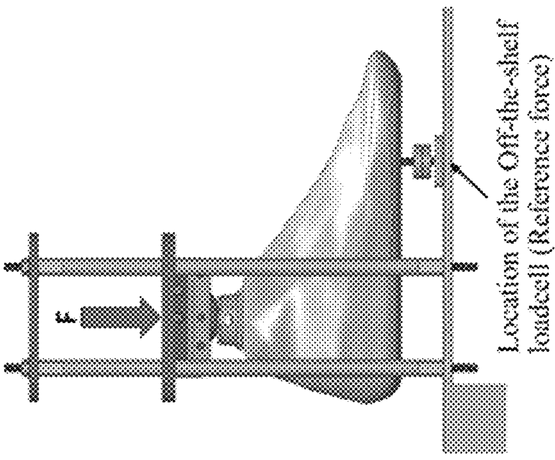
FIG. 10 illustrates an example benchtop testing setup for an example implementation of the present disclosure.
Figure 10:
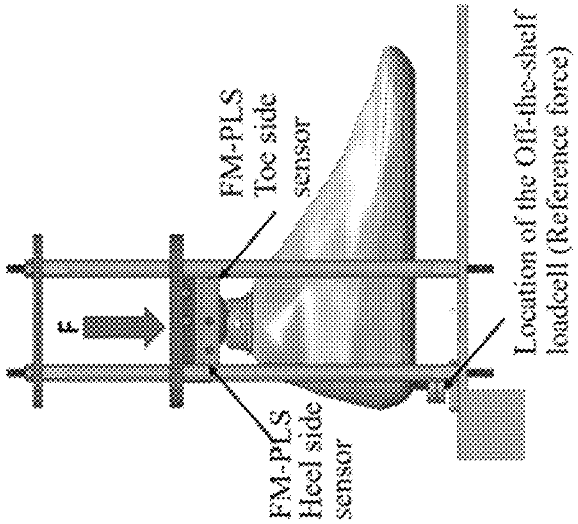
Figure 10:
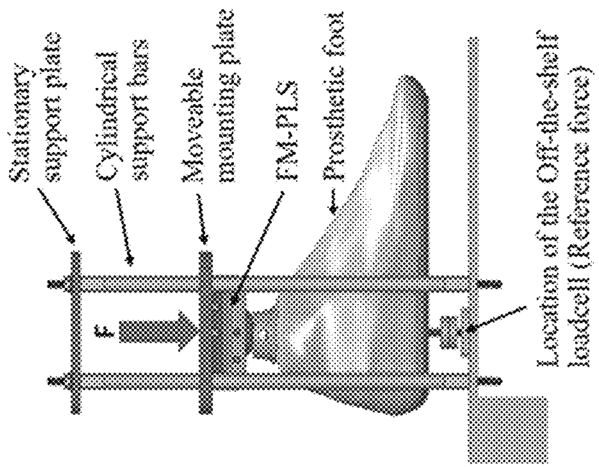

The goal of the benchtop testing was to monitor the loading response of the FM-PLS using an off-the-shelf loadcell as a reference measure. A testing setup was prepared for the benchtop testing of the FM-PLS in different loading conditions. The setup can include a stationary support plate, moveable mounting plate and four cylindrical support bars, as shown in FIG. 10. While the stationary plate is fixed on top of the cylindrical bars, the mounting plate can move freely through the cylindrical bars using four holes with the sleeve bearing inside. A lead screw mechanism was adopted in this setup to gradually apply force on the FM-PLS. The stationary plate provides support to the leadscrew mechanism, while the moving plate transfers force to the FM-PLS, attached to the bottom of the mounting plate. An off-the-shelf prosthetic foot was mounted with the FM-PLS. As a reference measure, an off-the-shelf loadcell was placed at different position underneath of the prosthetic foot while applying force from the top. In this experiment, the off-the-shelf loadcell was positioned at three location underneath foot peace, which are: (1) aligned with center of the FM-PLS, (2) at the heel of the prosthetic foot, and (3) at the toe (ball joint) of the prosthetic foot, as shown in FIG. 10.

The FM-PLS was fitted with a knee prosthesis to evaluate its performance. FM-PLS was interfaced with the prosthesis main controller unit, to feed the sensor signals to the controller. The prosthesis controller uses finite state impedance control strategy where real time gait events such as stance and swing phase detection can be used. FM-PLS data will be used in this experiment to identify those important gait events for the controller.

Figure 11:
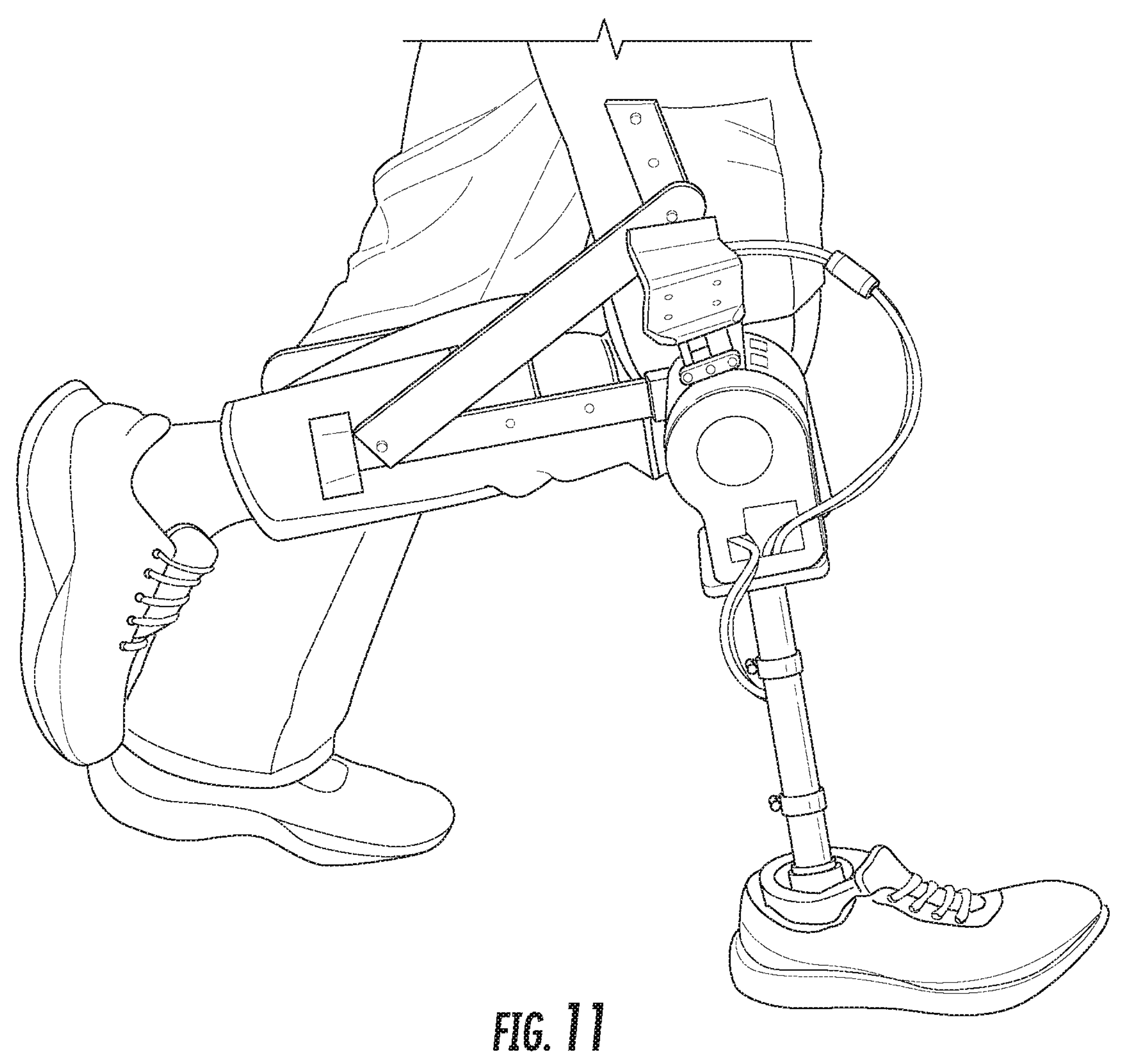
FIG. 11 illustrates a study of an example implementation of the present disclosure using a powered knee and treadmill.

An able-bodied male participant of age, height and weight are 31 years old, 175 cm and 70 kg respectively participated in the study. A commonly used able-bodied prosthesis testing adapter was used to attach the prosthesis to the subject. The experimental setup is shown in FIG. 11. The participant walked on treadmill at two different speeds (1 mph and 2 mph) while a total of 94 walking cycles were recorded.

Figure 12:
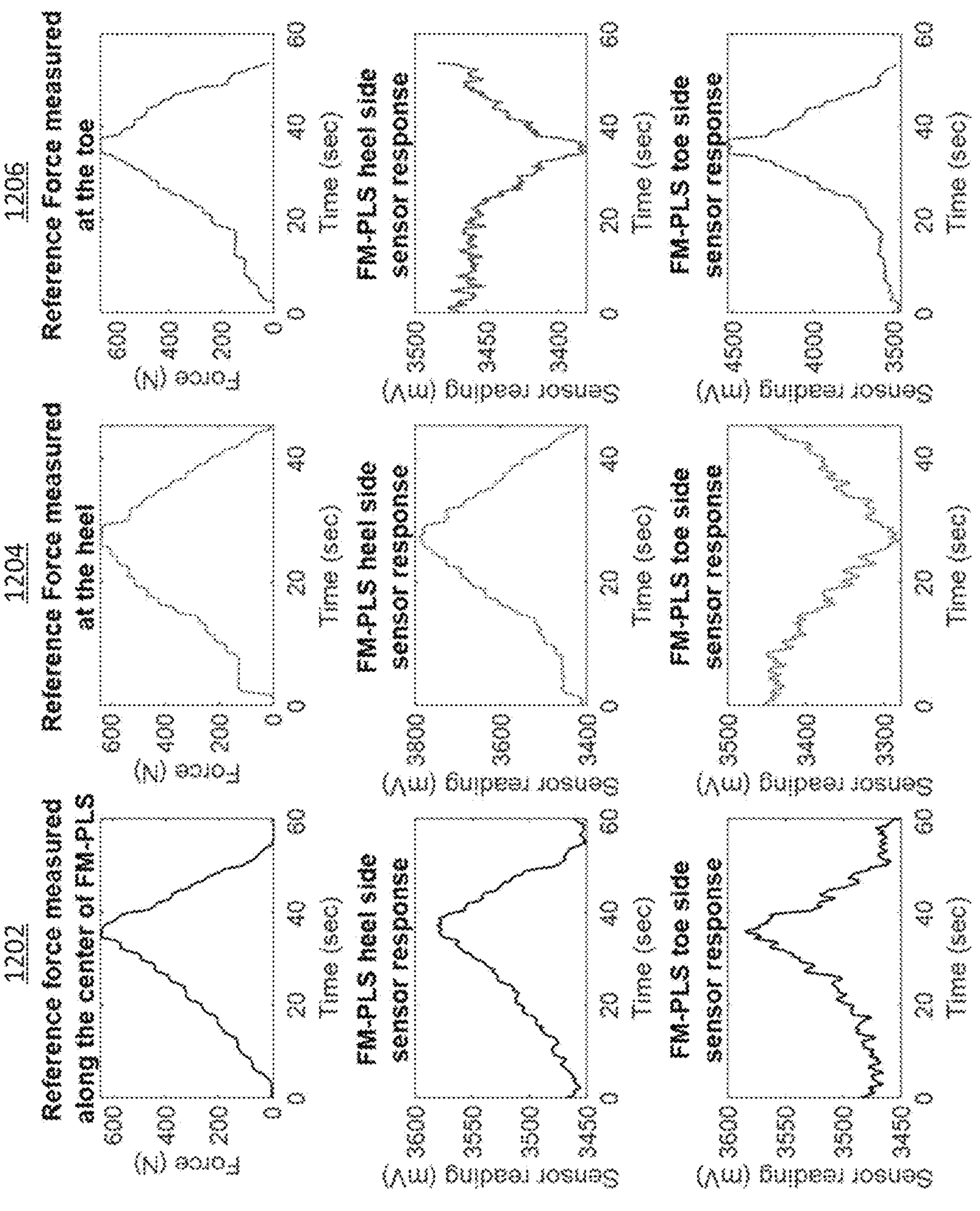
FIG. 12 illustrates a study including benchtop testing results for an example implementation of the present disclosure.

The results of the benchtop testing while placing the off-the-shelf loadcell underneath of the prosthetic foot as a reference measure are shown in FIG. 12. Both heel side and toe side magnetic flux sensor responses are depicted while the off-the-shelf loadcell was (1) aligned with center of the FM-PLS, as shown in a first column 1202 of FIG. 12. Further responses were recorded when the loadcell was (2) at the heel of the prosthetic foot and the results are illustrated in a second column 1204 of FIG. 12. Finally, further responses were measured when the load cell was aligned (3)

at the ball of the prosthetic foot and the results are shown in the third column 1206 of FIG. 12.

Figure 13:
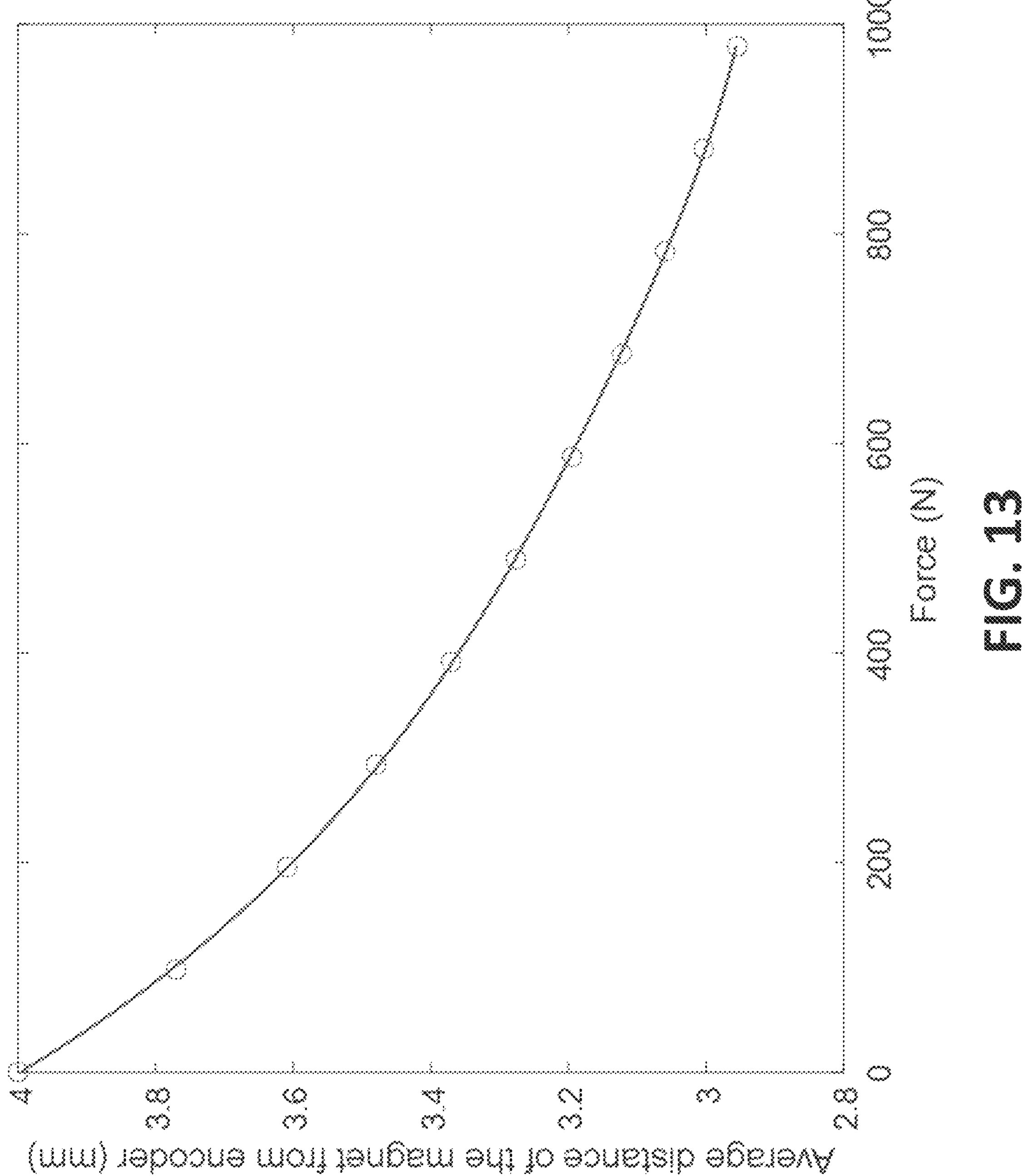
FIG. 13 illustrates study results including change of relative distance between a magnet and a magnetic field transducer with respect to the change of axial force, including $4^{th}$-order polynomial fitting.

Based on the FEA, FIG. 13 shows the change of relative distance between magnet and the magnetic field transducer with respect to the change of axial force, along with their $4^{th}$ order polynomial fitting. The figure shows that the $4^{th}$ order polynomial can express the force vs. distance relationship reasonably. The coefficients of the $4^{th}$ order polynomial model are as follows: 4.8069e−10, −2.8442e−07, 6.9600e−05, −0.01139, and 3.9971.

Figures 14A, 14B:
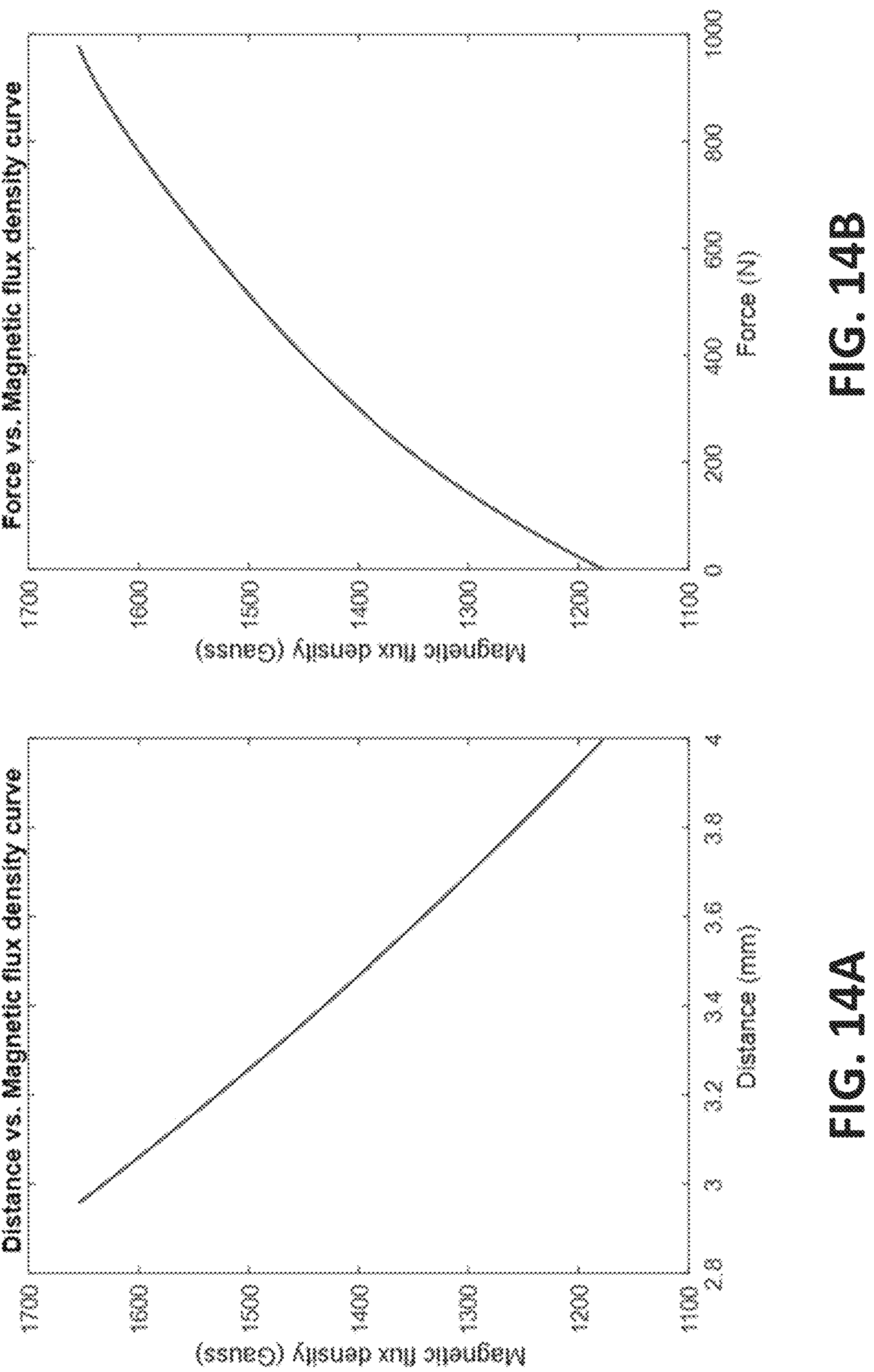
FIG. 14A illustrates a change of magnetic flux density with respect to the relative distance between magnets and magnetic field transducers, according to a study of an example implementation of the present disclosure.
FIG. 14B illustrates a study including a change of magnetic flux density with respect to axial force, according to a study of an example implementation of the present disclosure.

Based on Equation (1), FIG. 14A illustrates the change in magnetic flux density with respect to the relative axial distance between the magnet and the magnetic field transducer. By combining the force-distance relationship expressed by $4^{th}$ order polynomial model and the distance-magnetic field relationship given by Equation (1), the force-magnetic field relation has been established. Hence, the force vs. magnetic flux density can be described as shown in FIG. 14B. Since the voltage output of the magnetic field transducer is proportional to the magnetic field, thus force-magnetic field model can be converted to the force-voltage output model.

Figure 15A:
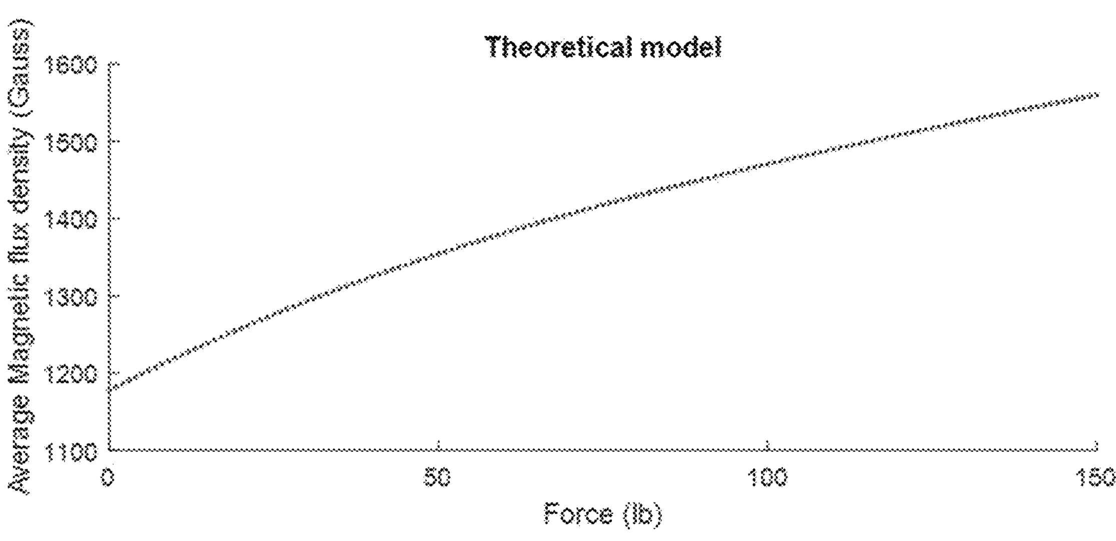
FIG. 15A illustrates a study of magnetic flux density based on a model of an example implementation of the present disclosure with respect to axial force change.
Figure 15B:
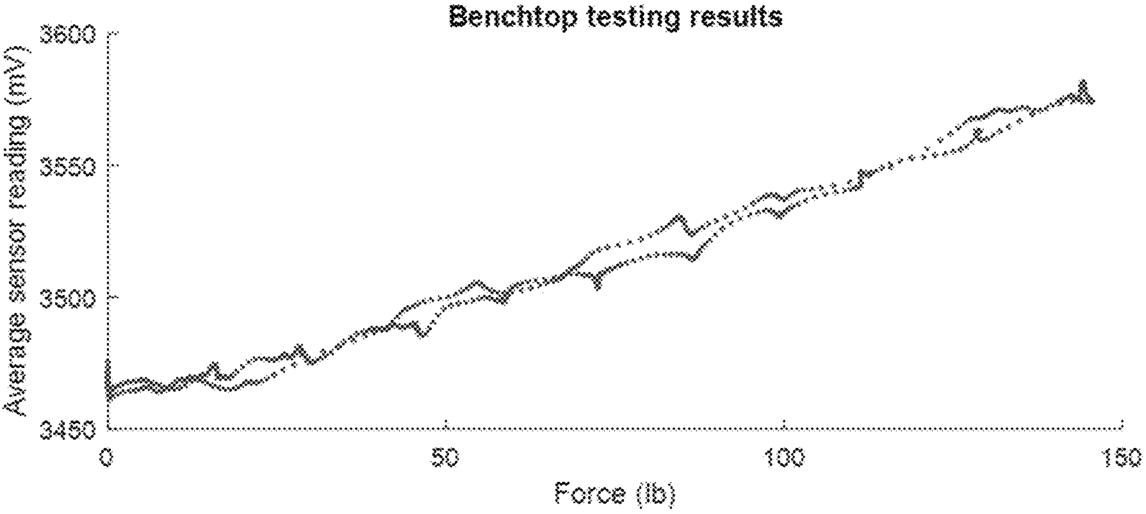
FIG. 15B illustrates a study of average sensor readings of an example implementation of the present disclosure with respect to the axial force change.

When the loadcell is positioned at the center, the applied load on the FM-PLS can be considered as the axial force. FIG. 15B shows the average sensor reading of the FM-PLS while the axial force was gradually increased from 0 N to 600 N (bottom figure). On the other hand, FIG. 15A shows the change in magnetic flux density based on the theoretical model developed for the similar axial force.

Figure 16A:
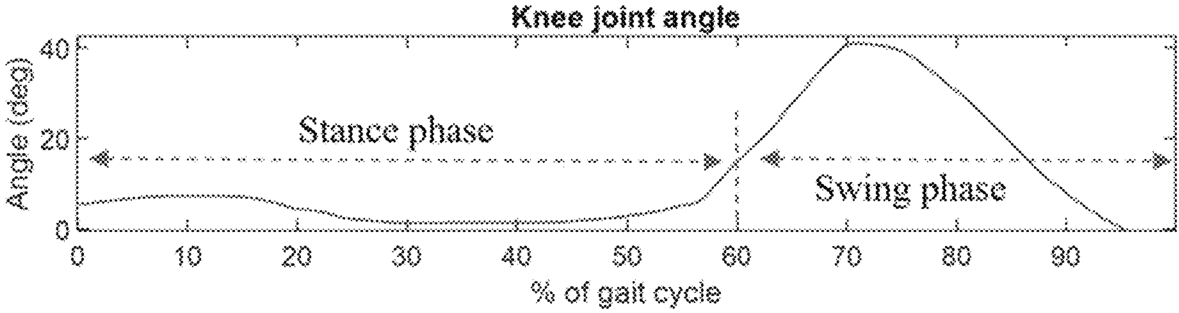
FIG. 16A illustrates a study of knee joint angle in a walking test of an example implementation of the present disclosure.
Figure 16B:
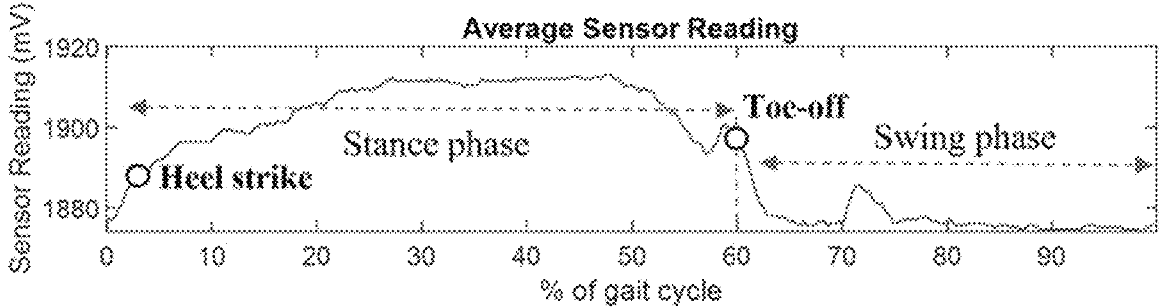
FIG. 16B illustrates a study of average sensor readings in a walking test of an example implementation of the present disclosure.
Figure 16C:
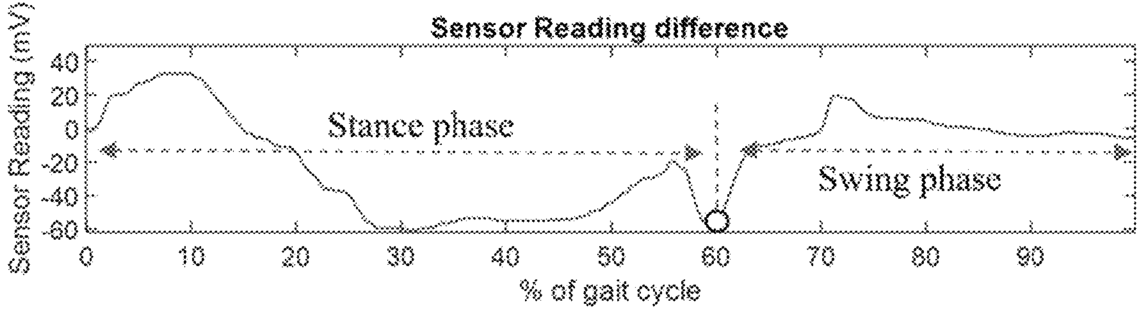
FIG. 16C illustrates a study sensor reading differences in a walking test of an example implementation of the present disclosure.

The results of FM-PLS prosthesis treadmill walking test are shown in FIGS. 16A-16C, which show the FM-PLS sensor response during a complete gait cycle along with the relative knee angle measured from the knee prosthesis encoder. As described herein, a complete walking gait cycle consists of stance phase (~60% of the cycle) and the swing phase (~40% of the cycle). The stance phase starts with heel contact and ends at toe-off. Hence the average sensor reading of the FM-PLS started to increase at the beginning of the cycle during the heel contact which clearly visible from the data shown in FIGS. 16A-16C. A threshold of 1890 mV was empirically selected based on the data for the heel strike detection and the prosthesis controller starts/switches stance phase when sensor reading is greater than the threshold. Conversely, the sensor reading drops immediately after the toe-off which is obvious from the result. The threshold for the toe-off was selected as 1895 mV below which controller switches to swing phase. Both of these thresholds were successfully used by the controller for the seamless switching between stance and swing phase without any misdetection during the prosthesis walking.

The example implementation described in the present study was compact and lightweight. The height of the device is only 2.5 cm which does not add too much build height to the prosthesis. The FM-PLS is compatible with pyramid adapter which can make it easier to attach with prosthesis without any design customization. The two-stage transduction using millimeter-scale deflection of a core elastic element makes the device more robust against interferences and drifting. The sensor does not require highly precise placement of magnets and magnetic flux as the sensor can easily tolerate misalignment. It should be understood that devices according to implementations of the present disclosure can have different dimensions from the example implementation described herein.

As shown in the benchtop testing results in FIG. 12, the device is sensitive at light load which makes it ideal candidate for prosthesis application due to its ability to identify heel contact during walking. Although the sensor is sensitive at light load, but it can still withstand heavy load (5000 N axial force) without structural failure, supported by the FEA analysis shown in FIG. 8. The bench top testing results validate the theoretical analysis by demonstrating similar curve between axial load vs. FM-PLS sensor response axial load vs. magnetic flux as shown in FIGS. 14A-14B. FIG. 14A illustrates a change of magnetic flux density with respect to the relative distance between magnets and magnetic field transducers, according to a study of an example implementation of the present disclosure.

FIG. 14B illustrates a study including a change of magnetic flux density with respect to axial force, according to a study of an example implementation of the present disclosure.

It should be understood that the load that can be sustained by the example implementation is intended only as a non-limiting example, and that different implementations of the present disclosure can be made of materials or structures that can withstand more or less axial load.

The prosthesis testing data shows that this device can identify the stance phase and swing phase. The average sensor reading started to rise immediately after the heel contact and drops after the toe-off as shown in FIGS. 16A-16C. FIG. 16A illustrates a study of knee joint angle in a walking test of an example implementation of the present disclosure.

FIG. 16B illustrates a study of average sensor readings in a walking test of an example implementation of the present disclosure.

FIG. 16C illustrates a study sensor reading differences in a walking test of an example implementation of the present disclosure.

Besides, sensor signals were used by the prosthesis finite-state-machine controller to successfully trigger the stance and swing phase which shows great potential of this device for real-time powered prosthesis control.

Moreover, the study shows that the example implementation of FM-PLS can be low cost. The cost of the mechanical and electrical components in the example implementation was ~$1000, which may even be reduced by mass production.

Unlike the existing strain gauge based loadcell, FM-PLS is based on the measurement of millimeter-scale deflection of a core elastic element, which provides stronger signals more robust against interferences and drifting. The FM-PLS example implementation can further incorporate the curved supporting blocks described which can modulate the deflection of the elastic member and thus make the measurement sensitive at light load yet withstanding heavy load without damage. The study described herein shows a two-stage transduction model to establish the relationship between input force/moment vs. output voltage. The benchtop testing results match reasonably with model-driven results. Additionally, the sensor was preliminarily validated for knee prosthesis walking tests. Results show that the proposed FM-PLS can detect important gaits events such as ground contact after leg swing and toe-off after stance phase which could be useful information for the intelligent motion control of the prosthesis.

CONCLUSION

It will be understood that each step of a method, block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

While this specification contains many specific implementation details, these should not be construed as limitations on the claims. Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein. It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

REFERENCES

1. Winter, D. A., *Biomechanics and motor control of human gait: normal, elderly and pathological*. 1991.
2. Orendurff, M. S., et al., *Gait efficiency using the C-Leg. Journal of rehabilitation research and development*, 2006. 43(2): p. 239.
3. Prinsen, E. C., et al., *The influence of a user-adaptive prosthetic knee across varying walking speeds: A randomized cross-over trial*. Gait & posture, 2017. 51: p. 254-260.
4. Thiele, J., et al., *Designs and performance of microprocessor-controlled knee joints*. Biomedizinische Technik/Biomedical Engineering, 2014. 59(1): p. 65-77.
5. Wu, M., M. R. Haque, and X. Shen, *Obtaining natural sit-to-stand motion with a biomimetic controller for powered knee prostheses*. Journal of healthcare engineering, 2017. 2017.
6. Gupta, S., *Strain gauge load cells*, in Mass Metrology. 2012, Springer. p. 89-119.
7. Pratt, D., et al., *Load measurement in orthopaedics using strain gauges*. Journal of Biomedical engineering, 1979. 1(4): p. 287-296.
8. Sup, F., A. Bohara, and M. Goldfarb, *Design and Control of a Powered Transfemoral Prosthesis*. The International Journal of Robotics Research, 2008. 27(2): p. 263-273.
9. Cherelle, P., et al., *Design and validation of the ankle mimicking prosthetic (AMP-) foot* 2.0. IEEE Transactions on Neural Systems and Rehabilitation Engineering, 2013. 22(1): p. 138-148.
10. Pandit, S., et al., *An affordable insole-sensor-based trans-femoral prosthesis for normal gait*. Sensors, 2018. 18(3): p. 706.
11. Rouse, E. J., L. M. Mooney, and H. M. Herr, *Clutchable series-elastic actuator: Implications for prosthetic knee design*. The International Journal of Robotics Research, 2014. 33(13): p. 1611-1625.
12. Gabert, L. and T. Lenzi, *Instrumented pyramid adapter for amputee gait analysis and powered prosthesis control*. IEEE Sensors Journal, 2019. 19(18): p. 8272-8282.

13. Lawson, B. E., et al., *A Robotic Leg Prosthesis Design, Control, and Implementation*. Ieee Robotics & Automation Magazine, 2014. 21(4): p. 70-81.

The invention claimed is:

1. A force-moment sensor for a prosthetic joint, comprising:

a first block having a first curved surface;

a second block having a second curved surface;

an elastic element arranged between the first block and the second block; and at least one sensing element configured to measure a deflection of the elastic element;

wherein at least one of the first curved surface and the second curved surface is configured to bend the elastic element when a force or a moment of force is applied to the force-moment sensor.

2. The force-moment sensor of claim 1, wherein the first block defines a first end and a second end opposite the first end, the first end comprising a first flat edge, wherein the second block comprises a third end and a fourth end opposite the third end, the third end comprising a second flat edge, and wherein the first and second blocks are arranged so that the first end of the first block is adjacent to the fourth end of the second block.

3. The force-moment sensor of claim 2, wherein the elastic element is fixedly attached to the first end of the first block and fixedly attached to the third end of the second block.

4. The force-moment sensor of claim 1, wherein the at least one sensing element comprises a plurality of sensing elements.

5. The force-moment sensor of claim 4, wherein a first sensing element and a second sensing element are arranged at opposite ends of the elastic element.

6. The force-moment sensor of claim 1, wherein the at least one sensing element comprises a magnetic sensor.

7. The force-moment sensor of claim 1, wherein the at least one sensing element comprises an inertial measurement unit (IMU).

8. The force-moment sensor of claim 1, wherein the at least one sensing element comprises a piezoelectric sensor.

9. The force-moment sensor of claim 1, wherein the at least one sensing element comprises a force-sensitive resistor.

10. The force-moment sensor of claim 1, wherein the elastic element comprises carbon fiber.

11. The force-moment sensor of claim 1, wherein the elastic element comprises fiberglass.

12. The force-moment sensor of claim 1, further comprising a plurality of bars, each of the respective bars being attached to the first and second blocks, wherein the bars are configured to limit a pulling force applied to the force-moment sensor.

13. The force-moment sensor of claim 1, further comprising a detachable adapter for operably connecting the force-moment sensor to a prosthetic device.

14. The force-moment sensor of claim 1, further comprising a housing.

15. A system comprising:

a prosthetic device comprising a first portion, a second portion, and a joint, the first portion and the second portion being joined by the joint; and a force-moment sensor arranged in the joint, the force-moment sensor comprising:

a first block having a first curved surface;

a second block having a second curved surface;

an elastic element arranged between the first block and the second block; and at least one sensing element configured to measure a deflection of the elastic element-;

wherein the first block defines a first end and a second end opposite the first end, the first end comprising a first flat edge, wherein the second block comprises a third end and a fourth end opposite the third end, the third end comprising a second flat edge, and the first and second blocks are arranged so that the first end of the first block is adjacent to the fourth end of the second block; and wherein the elastic element is fixedly attached to the first end of the first block and fixedly attached to the third end of the second block.

16. The system of claim 15, further comprising a computing device configured to: receive at least one sensor signal from the at least one sensing element; and determine a quantity of a force or a moment of force applied to the force-moment sensor based on the at least one sensor signal.

17. The system of claim 16, further comprising a motor configured to drive the prosthetic device, wherein the computing device is further configured to: control the motor based on the at least one sensor signal.

18. The system of claim 15, further comprising a computing device configured to: receive at least one sensor signal from the at least one sensing element; and distinguish between a force and a moment of force applied to the force-moment sensor based on the at least one sensor signal.

* * * * *